US012390655B2

(12) United States Patent
Sánchez Jaime

(10) Patent No.: US 12,390,655 B2
(45) Date of Patent: Aug. 19, 2025

(54) APPLICATOR HEADS, APPARATUS AND COSMETIC METHODS FOR TREATMENT OF SKIN OF A SUBJECT

(71) Applicant: HIGH TECHNOLOGY PRODUCTS, S.L., Barcelona (ES)

(72) Inventor: José Antonio Sánchez Jaime, Barcelona (ES)

(73) Assignee: HIGH TECHNOLOGY PRODUCTS, S.L., Barcelona (ES)

( * ) Notice: Subject to any disclaimer, the term of this patent is extended or adjusted under 35 U.S.C. 154(b) by 459 days.

(21) Appl. No.: 18/083,953

(22) Filed: Dec. 19, 2022

(65) Prior Publication Data

US 2023/0117411 A1 Apr. 20, 2023

Related U.S. Application Data

(63) Continuation of application No. PCT/EP2021/066559, filed on Jun. 18, 2021.

(30) Foreign Application Priority Data

Jun. 19, 2020 (EP) .................................... 20382536

(51) Int. Cl.
*A61N 1/40* (2006.01)
*A61B 18/00* (2006.01)
*A61B 18/14* (2006.01)

(52) U.S. Cl.
CPC .... *A61N 1/403* (2013.01); *A61B 2018/00291* (2013.01); *A61B 2018/00452* (2013.01); *A61B 2018/00577* (2013.01); *A61B 2018/00791* (2013.01); *A61B 18/14* (2013.01)

(58) Field of Classification Search
CPC .......... A61N 1/403; A61N 1/40; A61B 18/14; A61B 2018/00291; A61B 2018/00452; A61B 2018/00577; A61B 2018/00791; A61B 2018/142; A61B 2018/1467
USPC .................................................. 607/101, 108
See application file for complete search history.

(56) References Cited

U.S. PATENT DOCUMENTS

| 6,652,518 | B2 * | 11/2003 | Wellman ............... A61B 18/148 606/41 |
| 2004/0199228 | A1 * | 10/2004 | Wilson ................... A61B 8/546 607/101 |
| 2008/0269851 | A1 * | 10/2008 | Deem ...................... A61N 5/04 607/104 |
| 2012/0123411 | A1 | 5/2012 | Ibrahim et al. |
| 2013/0238062 | A1 * | 9/2013 | Ron Edoute ............. A61N 7/02 607/101 |

(Continued)

FOREIGN PATENT DOCUMENTS

| WO | 2007093998 A1 | 8/2007 |
| WO | 2008012827 A2 | 1/2008 |
| WO | 2014097288 A2 | 6/2014 |

OTHER PUBLICATIONS

International Search Report, PCT/EP2021/066559, Sep. 2, 2021, 3 pages.

*Primary Examiner* — Linda C Dvorak
(74) *Attorney, Agent, or Firm* — Edell, Shapiro & Finnan, LLC

(57) ABSTRACT

The present disclosure relates to devices and methods for cosmetic treatment of a skin of a subject with RF energy. Examples of the present disclosure include movable electrodes and/or movable skin temperatures sensors.

19 Claims, 11 Drawing Sheets

(56) References Cited

U.S. PATENT DOCUMENTS

| | | | | |
|---|---|---|---|---|
| 2013/0245727 | A1* | 9/2013 | Kothare | A61N 1/328 607/101 |
| 2013/0282085 | A1* | 10/2013 | Lischinsky | A61B 18/14 607/101 |
| 2014/0207217 | A1* | 7/2014 | Lischinsky | A61N 1/0492 607/101 |
| 2014/0249609 | A1* | 9/2014 | Zarsky | A61N 1/40 607/101 |
| 2014/0358200 | A1* | 12/2014 | Ko | A61N 1/328 607/101 |
| 2015/0080991 | A1* | 3/2015 | Britva | A61B 18/14 607/101 |
| 2015/0306419 | A1* | 10/2015 | Domankevitz | A61B 18/203 606/41 |
| 2016/0184602 | A1* | 6/2016 | Kim | A61N 5/02 607/101 |

* cited by examiner

APPLICATOR HEADS, APPARATUS AND COSMETIC METHODS FOR TREATMENT OF SKIN OF A SUBJECT

CROSS-REFERENCE TO RELATED APPLICATIONS

This application relates to and claims the benefit of priority to International Application. No. PCT/EP2021/066559, filed Jun. 18, 2021, which claims the benefit and priority to European Application No. 20382536.9, filed on Jun. 19, 2020.

FIELD

The present disclosure relates to methods and systems for treatment of skin of a subject involving applying electromagnetic energy, specifically radiofrequency (RF) energy, to the skin. The present disclosure more particularly relates to applicator heads, apparatus including such applicator heads and methods for treatment of skin of a subject including one or more movable electrodes and/or movable temperature sensors.

BACKGROUND

The aesthetic treatment of radiofrequency (RF) on the skin induces an electric current that circulates through the treated tissue. The term radiofrequency generally refers to an alternating current at high frequencies. The oscillation frequency may be e.g. 0.1 to 10 MHz, and specifically in a range of 0.1 to 5 MHz.

The resistance offered by the (skin) tissue to the passage of the current produces the transformation of RF energy into thermal energy. The transformation of electric current to thermal energy depends on different factors related to the characteristics of the treated tissue, as well as the characteristics of the RF energy, such as the power and the frequency, selected for the treatment.

Cosmetic effects that have been associated with an RF treatment include skin tightening and a local reduction of adipose tissue, i.e. fat. The treatments may be generally regarded as cosmetic rather than therapeutic.

These RF treatments wish to attain an effective treatment temperature while being safe. For instance, it is desirable to have a temperature sufficiently high in an area to be treated in order to obtain specific cosmetic results, e.g. 40-50° C., while at the same time damage, e.g. to the skin, is avoided or at least minimized. There is therefore a delicate balance between having a sufficiently high temperature to render the treatment more effective, while at those high temperatures the risk of a (local) burn of the skin increases. It is thus important to be able to precisely monitor the temperature or to have other security measures in place.

RF treatments may include monopolar and/or bipolar operation. If a first electrode is located in an applicator for an RF treatment and a second electrode is positioned on the subject's body, the current flows from the first electrode to the second electrode and it is said that the first and second electrodes operate in a monopolar mode. In this operational mode, the second electrode is known as passive electrode or return electrode. The passive electrode is generally positioned relatively far from the first electrode. As an example, if the applicator is placed on a subject's abdomen, the second electrode may be positioned on the subject's back.

Whereas in monopolar treatments a single electrode which continuously changes polarity is provided, two electrodes which continuously change opposite polarities are provided in bipolar treatments. In typical bipolar operation, the electric current flows from a first electrode to a second electrode and then from the second electrode to the first electrode. For instance, the applicator may have a first and a second electrode which may operate in bipolar mode.

The treatment achieved with a bipolar arrangement may be more superficial than with a monopolar arrangement. Multipolar (e.g. tripolar, tetrapolar, octipolar) arrangements are also known, in which three, four or more electrodes are provided. Typically, the plus and minus of these electrodes are controlled to create pairs of electrodes acting as a positive and a negative terminal.

In general, RF treatments may be performed by monopolar, bipolar and/or multipolar operation.

RF treatments are usually performed by an operator, e.g. a physician, which positions and moves an RF applicator along the skin of a subject. The operator is also typically in charge of selecting appropriate parameters, such as input power and/or frequency, and verifying that the treatment happens as planned, both in terms of effectivity and safety.

An RF treatment may last e.g. between 10 and 60 minutes. The longer the treatment, the more tiring it is for the operator to hold and move the RF applicator. Due to fatigue of the operator, unintentional mistakes, e.g. a skin burn by leaving the applicator on the same skin for a longer time than appropriate, may happen. Also, when the operator moves the applicator along a skin, some skin stops being treated because the applicator is no longer covering it. The larger the skin to be treated, the bigger this effect of non-homogeneity in the RF treatment becomes. At least these two aspects limit the efficiency and the safety of an RF treatment.

A way to increase safety during an RF treatment may be placing a temperature sensor in an electrode such that the temperature sensor measures a temperature when the electrode, and thus the temperature sensor, is in contact with the skin. However, measuring skin temperature with a temperature sensor which is both in contact with an electrode and the skin, has several drawbacks. Firstly, the temperature sensor acts as an obstacle to the RF energy applied through the electrode and thus the skin that is shielded or covered by the temperature sensor may not receive RF energy as desired. Secondly, non-shielded skin, especially in the vicinity of the temperature sensor, may receive more energy than expected as the temperature sensor may act as an energy diverter.

The present disclosure aims to provide improvements in devices and methods to enable more effective and safer treatments for the skin.

SUMMARY

In a first aspect, an applicator head for use with an apparatus for treatment of a skin of a subject is provided. The applicator head is configured for being fixed to the skin of the subject. The applicator head comprises a first radio frequency, RF, electrode, mounted on a first electrode support, wherein the first electrode support is movable with respect to a base of the applicator head such that a distance between the first electrode and a second electrode is varied in use.

A static applicator head is herewith provided that is able to perform a dynamic treatment to the skin due to the movement of the electrode support and the electrode embedded in the electrode support. Thus, an operator does not need to hold or move the applicator head along a skin of a subject during the treatment. At the same time, as the electrode in the electrode support may be continuously moving, this apparatus enables to heat the area to be treated in a more homogeneous way and also to reduce the risk of tissue injury, e.g. skin burn.

The second RF electrode may be included in the applicator head or in a neighboring applicator head. In such examples, the first and second electrodes may be operable in a bipolar mode. In some other examples, the second RF electrode may be a passive electrode configured to be located on a skin of a subject for monopolar operation, as explained further below.

The second electrode does not need to be movable with respect to the applicator head, as it is enough that one electrode, e.g. the first electrode, is movable for varying the distance between the first and second electrodes. However, both the first and second RF electrodes are movable with respect to the applicator head in some examples. This makes possible to cover a greater extension of skin during an RF cosmetic treatment, thereby enhancing the efficiency.

In these examples, the first RF electrode is mounted on the first electrode support, the second RF electrode may be mounted on a second electrode support, and the first and the second electrode supports may be movable with respect to the applicator head. Placing the first and second electrodes in different electrode supports increases the options of movement and ways of varying the distance between them. Again, due to the fact that both electrode supports are movable, this also facilitates to treat more skin and more constantly in comparison with having only one movable electrode support.

In the example above, the first electrode support may be operatively connected to the second electrode support, e.g. by meshing cogwheels or involving drive belts. For instance, an electrode support such as a rotatable plate may directly or indirectly engage with another electrode support such as another rotatable plate. This provides a dependence on the rotation of one of the plates with the rotation of the other plate.

The joint movement of the plates may be easier to configure and control when one or more plates are engaged.

One way to implement varying distances between the electrodes is to mount the first and/or second electrodes eccentrically in their electrode supports, i.e. by placing them towards an edge of an electrode support instead of in the center of the support. Thus, in some examples, e.g. in the example above, the first electrode is eccentrically mounted on the first electrode support.

The first and second electrode supports may include more than one electrode. In particular, in some examples, the first electrode support includes a first plurality of RF electrodes, and the second electrode support includes a second plurality of RF electrodes. Accordingly, the extension of skin and the frequency with which it may be treated is increased. Including more electrodes also offers a higher versatility, as the electrodes through which RF energy may be applied during an RF cosmetic treatment may be changed and adapted to the needs of the subject.

The movement of the electrode support(s) and the electrode(s) embedded therein may be any suitable type of movement. For instance, the electrode support(s) may be configured to move linearly and/or circularly. In an example, one or more electrode supports include plates configured to rotate around an axis of rotation substantially perpendicular to the plate. Configuring the plate(s), or in general the electrode support(s), and the embedded electrode(s) to perform a rotational movement enables to perform a treatment encompassing a wider area of the skin.

In some examples, the applicator head defines a cavity for receiving a portion of the skin of the subject and further comprises a suction orifice configured to be coupled to a pump for sucking air through the suction orifice. The suction orifice enables to suck a portion of the skin into the cavity of the applicator head and to provide a better contact between the skin and the electrodes. This may help to provide a more effective treatment and to reduce local burns to the skin. Suction may also provide a stronger attachment of the applicator head to the body of the subject. The cavity may be static, and the electrode support may be movable or rotatable with respect to the cavity.

In such an example, the applicator head may further comprise a flexible lip arranged along a border of the cavity for sealing the cavity. Throughout this disclosure, a lip may be regarded as a flexible material which may be placed over a border or edge of an applicator head for better adapting to the curves of the body and thus better sealing the cavity. This may facilitate and enhance suction.

The applicator head may be configured to be fixed in place. To do so, it may comprise one or more mechanical fasteners to fix the applicator head to the skin. In some examples, the fasteners include one or more straps. Suction may be used, in combination with one or more mechanical fasteners or in a standalone mode, as fixing means too.

The various fixing means enable performing an RF treatment without the (continuous) presence of an operator. Also, safety is improved due to the fact that mistakes due to human manipulation of the applicator head can be avoided or at least reduced. As an example, with this applicator head an operator does not need to hold and move it for performing the treatment and accordingly he/she would not inadvertently overheat the skin by leaving the applicator head on the same place for too long. This particularly applies the longer the treatment is. For instance, an operator will get more tired when the treatment lasts 30 minutes than when the treatments lasts 10 minutes. Thus, in the first case, there is a greater risk that an operator makes a mistake. Accordingly, this applicator head also enables the performance of a safer treatment.

In a further aspect, an apparatus for treatment of a skin of a subject comprising one or more applicator heads as disclosed above and through the corresponding examples and claims is provided. In an example, two or more applicator heads may be used for an RF treatment without human intervention while the treated area increases with respect to using only one applicator head. The applicator heads may further comprise a drive for moving the first electrode support and an electrical power source for supplying electricity to at least the first electrode. In general, the apparatus may move one or more electrodes and one or more electrode supports, including all electrodes and all electrode supports. Likewise, electricity may be supplied to any number of electrodes comprised in an applicator head or in an apparatus, including all the electrodes.

In yet a further aspect, a method for treating a skin of a subject is provided. The method comprises: providing an apparatus as disclosed herein, attaching one or more applicator heads to a skin of the subject, putting a portion of the skin and one or more applicator heads into contact, activating the drive for moving the first electrode support; and activating the electrical power source to supply RF energy to the skin.

As indicated, the method may be particularly cosmetic, i.e. non-therapeutic. Non-therapeutic as used herein implies that the method does not aim or achieve the curing of a disease or malfunction of the body. Rather, this cosmetic method provides a localized effect of skin tightening or reduction of fat tissue, e.g. subcutaneous fat and/or cellulite. This applies to all the methods mentioned throughout this disclosure. I.e., all the methods are cosmetic methods and refer to cosmetic treatments.

RF energy may be applied to the skin through at least the first moving electrode. The above method delivers a dynamic RF treatment through one or more static applicator heads. Therefore, heat may be uniformly distributed in the totality of the treated area while possible mistakes linked to human movement of the head during the treatment, e.g. skin burn, are avoided or at least reduced.

Also, due to the movement of the electrodes, and also e.g. to protrusions and recesses of the applicator head, the skin is also massaged.

In some examples, the second electrode is a passive electrode and is located on the skin of the subject. Accordingly, the first and the second electrode are operating in a monopolar configuration. Herein, the generated heat density between the first and the second electrodes, which in an example may be in contact with an abdomen and a back of a subject, respectively, is continuously moving due to at least the movement, e.g. rotation, of the first electrode. Therefore, different regions are heated overtime and thus a specific region is not overheated and burn risk is minimized. The distance between the first and second electrodes is not only varied due to the displacement of the first electrode over the skin, but also due to the curves and folds of the skin which are moved and/or pressed when at least the first electrode is in contact with them. The skin may be then moved in several directions, hence modifying the distance between the first and second electrodes also in a monopolar treatment.

In some examples, the second electrode has an opposite polarity from the first electrode polarity, the first and second electrodes form a first pair of electrodes and RF energy is applied to the skin through at least the first pair of electrodes. The first and the second electrode are then operating in a bipolar configuration. In this case, the movement of the electrodes makes it possible to cover and treat a bigger portion of skin. Also, the electrode movement avoids hot spots, which are undesirable as they may burn the skin. In addition, as the distance between electrodes is varied due to the movement of at least the first electrode, the penetration depth of the treatment is modified too continuously throughout a treatment. A usual way to change the penetration depth is by e.g. modifying the frequency, but this method enables to change the penetration depth by keeping the same value of frequency. Accordingly, more combinations of attainable penetration depths and frequency become available and the method may be more controllable and tunable.

A greater skin extension and depth can be treated with this method in a safer way. In some examples, the apparatus operates in both a monopolar mode and a bipolar mode, e.g. alternatively. The advantages linked to each operation mode are then obtained. In general, any combination of unipolar, monopolar, bipolar and multipolar (i.e. tripolar, tetrapolar, octipolar) RF treatments may be used.

In some examples, the second electrode is located in the applicator head including the first electrode. In other examples, the second electrode is located in an applicator head different from the applicator head comprising the first electrode. These two configurations indicate that bipolar operation may take place in the same applicator head and/or between different applicator heads. It shall be understood that if the first electrode in these two configurations is the same, these configurations occur in different times. But it is also possible to apply RF energy through a pair of electrodes in a first applicator head and through another pair of electrodes having an electrode in the first applicator head and the other electrode in a second applicator head simultaneously if no electrode is shared between these pairs. Applying RF energy through at least an electrode pair having an electrode in one applicator head and having the other electrode in another applicator head enables to treat skin between the applicator heads.

In some examples, the method further comprises interrupting the application of RF energy to a skin through the first pair of electrodes, and applying RF energy to the skin through a second different pair of electrodes such that RF energy is applied at least to a partially different skin.

This enables creating different paths for the RF energy in the same applicator head and/or between different applicator heads. Accordingly, a more tailored treatment to the region to be treated and even to the particularities of the subject to be treated may be obtained. For example, a specific number and position on the skin of applicator heads may be selected for the treatment, and the electrodes applying RF energy at a certain time may be modified along the treatment. A more effective and safer method may thus be provided.

In some examples, the method further comprises joining a first and at least a second applicator head. The joining of applicator heads, e.g. forming a chain or other arrangement around a thigh or a waist, facilitates to treat a wider region of a skin during the same treatment.

In some examples, at least two electrode supports move at the same speed, in particular at the same rotational speed. Due to the same speed of the electrode supports, a more homogenous and controllable treatment takes place.

In yet a further aspect, an applicator head for use in an apparatus for treatment of a skin of a subject is provided. The applicator head comprises an electrode support comprising a radio frequency, RF, electrode and a skin temperature sensor adjacent to the electrode. The electrode support is movably mounted with respect to a base of the applicator head.

Including a skin temperature sensor that is movable jointly with at least an electrode enables to detect an average temperature of a skin being treated during an RF treatment. This is due to the fact that at least an electrode moves along the skin and the skin temperature sensor "following" the electrode. The temperature measured with the sensor is not directly the temperature of the electrode, nor only of the skin directly receiving the heat of the electrode. Thus, a temperature measured by the skin temperature sensor may correspond to an average value of the temperature of the skin affected by the movement of the electrode. The measured average skin temperature may be used to at least partially control and adjust the RF energy applied through the electrode(s).

Also, as the skin temperature sensor is adjacent to the electrode, i.e., close to the electrode but not in contact with it, an interference of the current between electrodes, e.g. in bipolar operation, is avoided. If the skin temperature sensor was placed in contact with the electrode, a measured value of skin temperature would not be representative of the energy applied through the electrode since the skin temperature sensor would be actually blocking the passage of energy from the electrode to the skin.

In some examples, the applicator head further comprises at least an additional electrode and the skin temperature sensor is also adjacent to at least the additional electrode. In this case, the contribution of both electrodes to an average skin temperature may be measured.

In some examples, the applicator head further comprises at least an additional skin temperature sensor adjacent to one or more electrodes. Measurements from more than one skin temperature sensor may increase the reliability of the measured temperature values.

In some examples, the applicator head further comprises an electrode temperature sensor in contact with an electrode. This electrode temperature sensor is configured to measure an electrode temperature and not a skin temperature, like the skin temperature sensor. I.e., whereas the skin temperature sensor is configured to be in contact with a skin of a subject, the electrode temperature sensor is not. In some examples, the electrode temperature sensor may be in contact with an internal surface of the electrode. An internal surface of the electrode is a surface of the electrode which is not configured to be in contact with a skin.

An electrode temperature sensor may be used to detect whether the electrode temperature is exceeding a threshold electrode temperature. A threshold electrode temperature may such that, if exceeded, damage may occur to a treated region of a subject. Damage may include skin burn.

In yet a further aspect, an apparatus for treatment of a skin of a subject comprising one or more applicator heads as disclosed in the above paragraphs and corresponding examples and claims is provided. The apparatus includes an electric power source and a control system for controlling electrical energy supplied to at least one of the RF electrodes.

In yet a further aspect, a method for treating a skin of a subject is provided. The method comprises providing an apparatus for treating a skin of a subject, putting a portion of a skin and an applicator head into contact, moving an electrode support with respect to a skin of the subject, applying radio frequency (RF) energy to the skin through an electrode, measuring an average skin temperature of a portion of the skin, and adjusting the RF energy applied through the electrode at least partially based on the measured average skin temperature.

This method allows measuring an average skin temperature of a region of tissue being treated by the moving electrode and to adjust the RF energy provided through the electrode. This method may be performed by an operator, e.g. if the operator holds the applicator head, or may be performed without an operator, e.g. if the applicator head is fixed to the skin of the subject by fixing means.

In some examples the adjusting includes adjusting at least one of: power and frequency. For instance, adjusting one or more magnitudes may comprise varying a value of power and/or frequency. It is noted that adjusting does not necessarily imply changing the value of a magnitude. For example, adjusting includes not modifying one or more (even all) the values of the magnitudes. Accordingly, in some examples, adjusting one or more magnitudes may comprise keeping the values of power and/or frequency.

In some examples, the method further comprises determining or programming a reference average skin temperature, specifically wherein the reference average skin temperature is between 40 and 50° C.; and adjusting, by a control system, the RF energy applied through the electrode based on a measured average skin temperature to maintain the average skin temperature close to the reference average skin temperature.

The use of a measured average skin temperature to maintain the average skin temperature close to the reference average skin temperature, e.g. during all the RF treatment, increases the security of the RF treatment. Injuries to the tissue, e.g. skin burn, may thus be reduced or avoided while an effective RF treatment is performed. In some examples, the reference average skin temperature may range between 40 and 50° C.

In some examples the method further comprises measuring the temperature of an electrode by an electrode temperature sensor, and when the measured electrode temperature exceeds an electrode temperature threshold, at least decreasing the energy applied through the electrode and/or interrupting the energy applied to the electrode.

This may provide an additional security measure. For instance, if the electrode temperature becomes so high that the skin may be burned, the energy applies through the electrode is decreased. If this energy reduction is not enough, this energy application through the electrode may be interrupted, e.g. by switching off an RF energy source.

In some examples, the reference average skin temperature and/or the electrode temperature threshold range between 40° C. and 50° C. This enables to have both an effective and safe RF treatment.

In some examples, monopolar, bipolar and/or multipolar operation may be included in the RF treatment.

In some examples, the RF treatment may last between 10 and 60 minutes.

The above apparatuses and methods in general provide a more effective and safer RF treatment. A substantially uniform RF energy distribution with a power per surface unit with respect to a manual treatment performed by an operator holding a moving an RF applicator may be obtained.

The present disclosure provides devices, systems, apparatus and methods with a concept of moving electrodes, in which a distance between electrodes may be varied. The present disclosure also provides devices, systems, apparatus and methods relating to a concept with a skin temperature sensor aimed at measuring an average skin temperature. Different embodiments of both these concepts are disclosed. The concepts may be used separately or in combination.

BRIEF DESCRIPTION OF THE DRAWINGS

Non-limiting examples of the present disclosure will be described in the following, with reference to the appended figures, in which.

The figures refer to example implementations and are only be used as an aid for understanding the claimed subject matter, not for limiting it in any sense.

DETAILED DESCRIPTION

Figure 1:
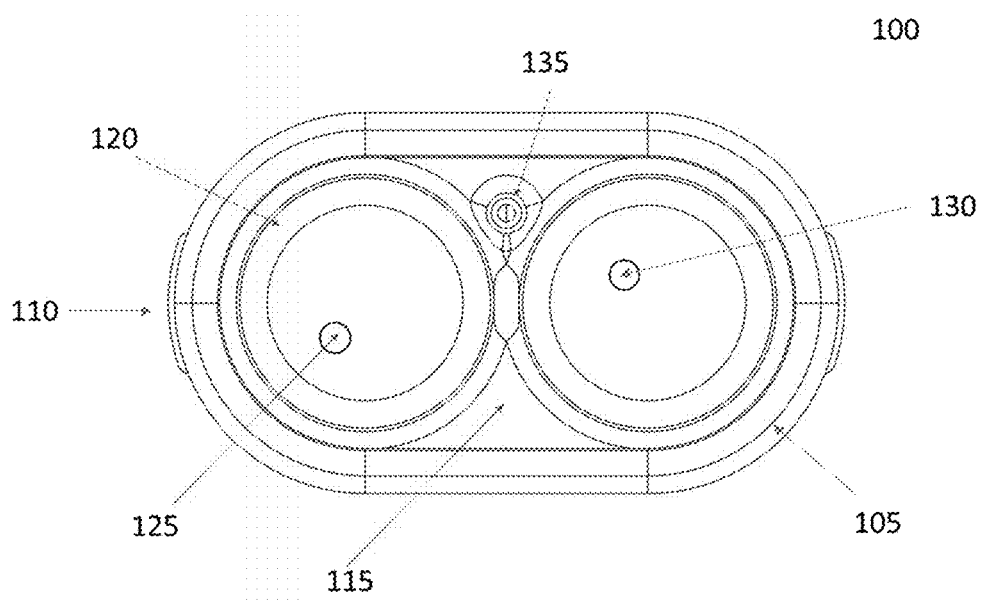
FIG. 1 schematically illustrates an example of an applicator head which may be used in an apparatus for treatment of a skin of a subject.

FIG. 1 schematically represents an applicator 100 for an apparatus for treatment of a skin of a subject. An apparatus may comprise a base station and one or more applicators. Each of the applicators may be adapted to different parts of the body of a subject. Each of the applicators may be connected to the base station through a tube. The tube may include electrical cables for providing electrical power from the base to the applicators, an air conduit leading from a pump to the applicators, and data transmission cables for transmission of control signals. The applicator 100 comprises an applicator head 110 that, in this example, defines a cavity 115 for receiving a portion of the skin of the subject.

In this example, the first applicator head 110 comprises two electrode supports 120 which are movably mounted with respect to a base of the applicator head 110. In general, an apparatus may include one or more applicator heads 110, and an applicator head 110 may include one or more electrode supports 120. In FIG. 1, the two electrode supports 120 are circular plates configured to rotate around an axis of rotation substantially perpendicular to the corresponding plate. In this or another example, an electrode support 120 may have a diameter of between 60 and 70 mm. Other shapes, e.g. rectangular or squared, are also possible for an electrode support 120 in an applicator head 110. Although in this example the two plates have the same size, if there is more than one electrode support 120 included in an applicator head 110, they may have different sizes too.

An applicator head 120 may include an applicator head base and one or more applicator head sidewalls. In FIG. 1, the two electrode supports 120 are rotatably mounted to the applicator base. In some other examples, one or more electrode supports 120 may be mounted to any of base and/or a sidewall.

In FIG. 1, each electrode support 120 includes an RF electrode 125, 130. For illustrative purposes, one may consider electrode 125 to be a first electrode 125 and electrode 130 to be a second electrode 130. The first electrode 125 is movable such that a distance between the first electrode 125 and the second electrode 130 is varied.

The fact that a distance between a first electrode 125 and a second electrode 130 may be varied makes it possible to treat a larger area of tissue in a safer way.

In monopolar operation, RF energy may be applied though a first electrode 125, whereas a further electrode is arranged somewhere on the patient. E.g. the first electrode 125 and applicator 100 may be positioned on a stomach area of a subject, whereas the further electrode may be positioned on the subject's back.

The rotation of the first electrode in monopolar operation is such that different regions of tissue are heated over time due to movement of the electrode 125 and due to the movement of the skin that is e.g. displaced, pressed and/or massaged by the electrode 125. This effectively heats a larger portion of tissue while minimizing overheating which may cause e.g. skin burns.

In bipolar operation, a larger area or region of tissue is heated more homogeneously thanks to the movement of the electrode(s) 125, 130. If a distance between the electrodes is continuously changed, a depth of treatment is also continuously changed. In addition, RF frequency may be varied in some examples. A finer control of the RF treatment can be achieved as the number of combinations of values of penetration depth and frequency that can be used is higher with this apparatus. Continuous movement can provide for a large treatment area and hot spots may be avoided due to this electrode movement. Accordingly, damage to the skin, such as skin burns, may be avoided too.

In the current example, both the first electrode 125 and the second electrode 130 are movable by the corresponding electrode supports 120. In some other examples, the second electrode 130 may not be movable and/or may not be included in an electrode support. For instance, in some examples, the second electrode 130 may be embedded in a sidewall of an applicator head 110. In these or other examples, the second electrode 130 may be a passive or return electrode 130 configured to be positioned on the skin of a subject, e.g. for monopolar operation.

It shall be understood that a movable electrode may be a first electrode 125, and that any other electrode whose distance to a first electrode 125 may be modified due to the movement of the first electrode 125, may be considered a second electrode 130. For example, if the electrode support 120 including the second electrode 130 in FIG. 1 would include more electrodes, all of them would be second electrodes 130 with respect to the first electrode 125. If in addition to this, if the apparatus 100 included a return electrode for monopolar operation, this electrode would also be a second electrode 130. Accordingly, an apparatus 100 may operate in any of a unipolar, monopolar, bipolar and/or multipolar mode.

The number of electrodes that an electrode support 120 may comprise is variable within the scope of the present disclosure. For instance, a movable electrode support 120 may include one, two, three or more electrodes. It may also happen that one or more electrode supports 120 include zero electrodes.

The applicator 100 also comprises means 105 to attach the applicator head 110 to the body of the subject. In FIG. 1, this can be a flexible lip 105 covering the edge of the applicator head 110 which delimits the opening of the applicator head 110 for receiving a skin of a subject. The lip may be made of e.g. plastic or silicone, and may provide fixation to the skin of a subject by applying vacuum to the treated region by providing a sealing attachment. The lip may be removable from the applicator head 110 and may also be washable.

In other examples, additionally or alternatively, some mechanical fasteners may be provided to fix the applicator head 110 in place. For example, one or more straps, e.g. leather or plastic straps may be used. One or more straps may be attached to the applicator head or may be provided separately from the applicator head and be guided by e.g. eyelets on the applicator head 110. Other fixing means may be used. More than one type of fixing means may also be used. For instance, in some examples a lip and a strap may be used.

The fastening means or attachment means 105 enables that an apparatus head 110 is attached to the skin of a subject such that the apparatus head 110 remains in place during an RF treatment without the need to have an operator holding and/or moving the applicator head 110 along the skin of a subject. Mistakes due to tiredness and/or distraction of an operator handling an applicator head 110 may thus be avoided.

An electrode support 120 may be operatively connected with another electrode support 120 e.g. by including meshing cogwheels. By cogwheels or other gears engaging with each other, the electrode supports 120 move in a co-dependent manner. By doing so, the effect of the movement of the electrode supports 120 is more predictable on the heat distribution in the tissue and thus the configuration and control of the apparatus 100 may be easier. In some examples, one or more electrode supports 120 are in operative connection with each other. In some other examples, no electrode support 120 is operatively connected with another electrode support 120.

Further alternatives for operatively connecting electrode supports which may be incorporated in any of the examples may include a belt or chain drive.

Applicator head 110 also includes a suction recess 135, in particular a suction hole. A suction recess 135 can be coupled to a pump to reduce a pressure in the cavity 115 (i.e. creating a negative pressure) of the applicator head 110. Therefore, a portion of a skin of the subject may be sucked into the cavity 115. Additionally or alternatively, a vacuum may be created in order to attach the applicator head 110 to the skin of the subject.

Throughout this disclosure, a negative pressure or vacuum may be regarded as a negative pressure of 0.6 to 1 atm, and specifically a negative pressure of 0.7 to 0.98 atm. The pressure in the cavity 110, when in use may particularly be in the range of 0.02 to 0.3 atm (20 to 270 mbar).

The negative pressure applied to the skin also improves or ensures the contact between the skin and RF electrodes. This can reduce local burns of the skin and enables massaging the skin in the cavity when the electrodes are moving. An applicator head 110 may have protrusions and/or recesses, e.g. in an applicator head 100 sidewall. These protrusions and/or recesses might contribute to the massage.

Figure 2:
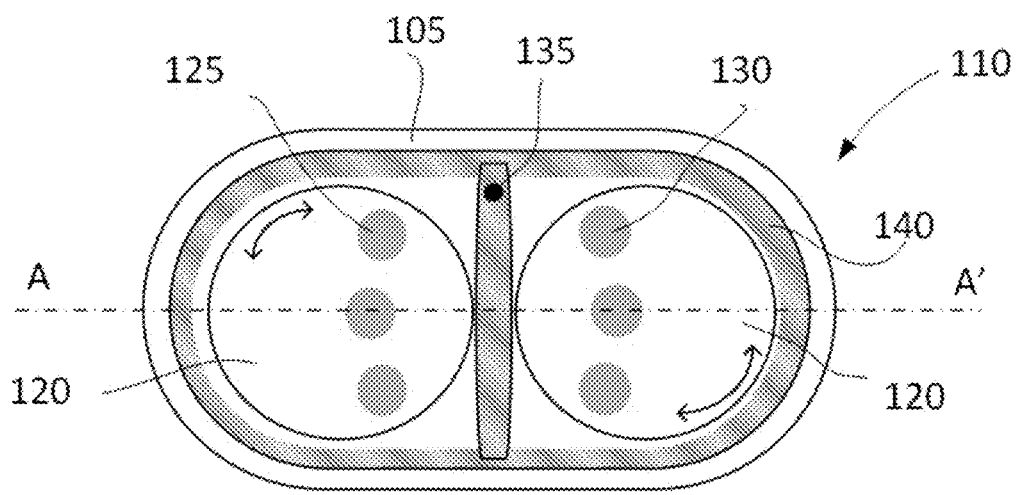
FIG. 2 schematically illustrates another example of an applicator head.
Figure 3:
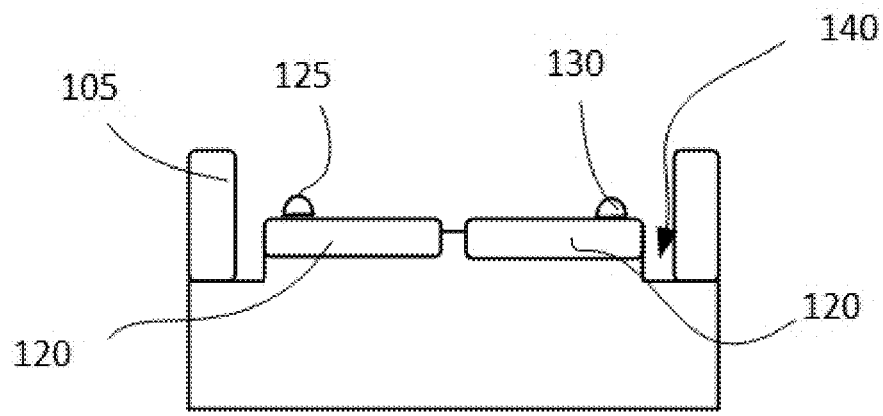
FIG. 3 schematically represents a sectional view of the applicator head of FIG. 2 along line AA'.

FIGS. 2 and 3 shows a schematic representation of another example of an applicator head 110. Three electrodes are included in each rotatable electrode support 120 in FIG. 2. In an example, the distance between the more external electrodes may be between 45-50 mm and the distance between an external electrode and the central electrode may be between 25-30 mm.

In FIG. 2, the applicator head 110 includes a channel 140. Channel 140 improves the attachment of the applicator head 110 to the skin and enables more tissue to enter the cavity 115. In this example, each electrode support 120 includes three electrodes. The black curved arrows in FIG. 2 indicate the possible directions of rotation of each electrode support 120. The depth of channel 140 may be better appreciated in FIG. 3. FIG. 3 illustrates a transversal cut of an applicator head 110 like the one in the example of FIG. 2 along the line AA' of FIG. 2. A removable lip 105 is also shown. A height of a lip 105 may vary along the perimeter of the applicator head 110. This can facilitate the adaptation of the lip to the curves of the body.

Preferably, the electrode supports are in continuous rotation in the same direction (which might be different for different electrode supports), so as to avoid interrupting rotation.

FIG. 3 also shows that electrodes may be convex. Curved electrodes favor skin deformation over them and improve the coupling to the skin. This also reduces the formation of high-density current regions which may cause hot spots. Therefore, skin burns can be reduced. In FIG. 3, electrodes 125 are partly spherical. In other examples, electrodes may be squared with rounded edges. The combination of different shapes of electrodes in a same applicator head 110 is also possible. Throughout this disclosure, electrodes may be made from a variety of materials, e.g. stainless steel and/or aluminum. Electrodes may be coated with a layer of anodized aluminum or any other semiconductor material. Electrodes may be refrigerated by liquid or gas circulation or by contact with a cool plate of a peltier cell.

Figure 4:
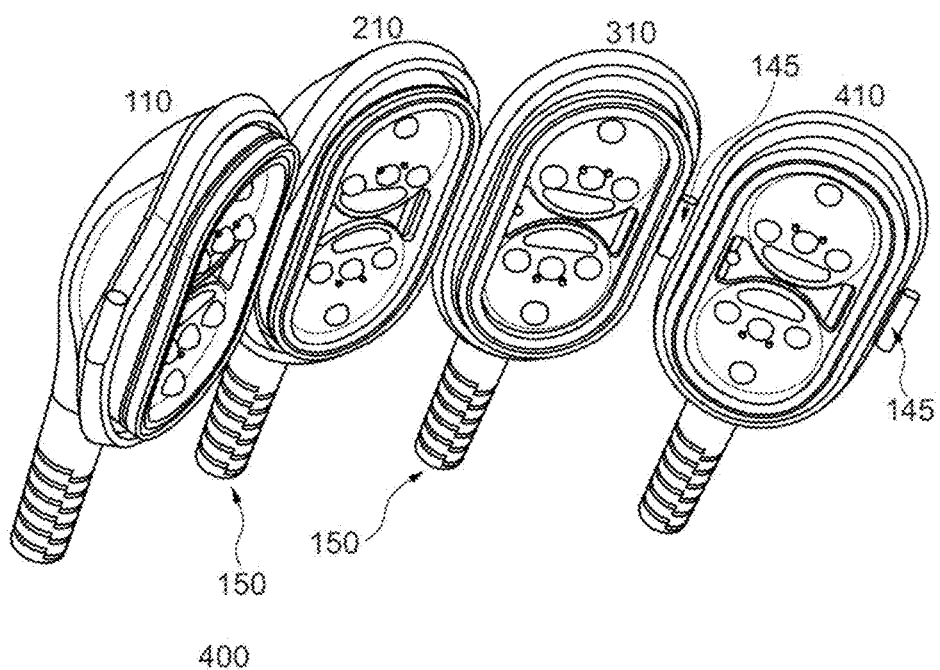
FIG. 4 schematically illustrates an example of an apparatus for treatment of a skin of a subject.
Figure 5:
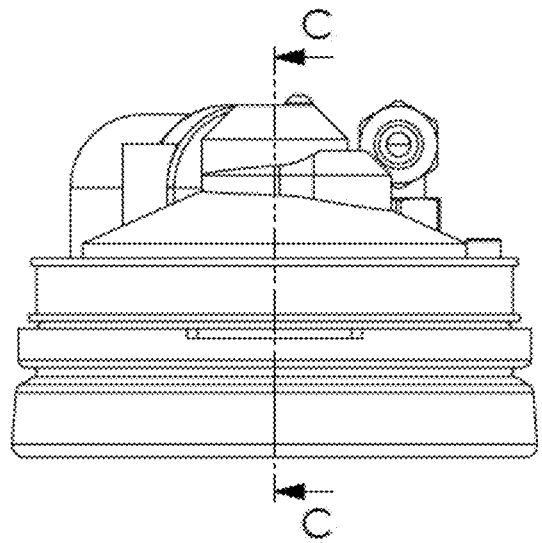
FIG. 5 schematically represents a side view of an applicator head.

FIG. 4 shows another example of a portion of an apparatus 400. Apparatus 400 includes more than one applicator head 110. In particular, apparatus 400 includes four applicator heads 110, 210, 310 and 410. In FIG. 5, these applicator heads 110, 210, 310, 410 are joined to each other by fastening means 145 located on a lateral of the applicator heads 110, 210, 310, 410. The fastening means 145 may be male and female connectors in FIG. 4. In general, an applicator head may include one or more fastening means 145 placed in different locations. In FIG. 4, the joined applicator heads 110, 210, 310, 410 form a chain that may be placed around e.g. an arm or a thigh. But in some other examples, one or more applicator heads may include additional fastening means 145 such that the joined applicator heads form a square, e.g. to cover an abdominal region of a body. Accordingly, the use of two or more applicator heads 110 enables to treat a greater extension of skin. In order to do this, one or more applicator heads may not be attached between/among them in some other examples. Also, one or more applicator heads may not include fastening means 145.

The fastening means 145 may also include magnetic means, mechanic means and/or adhesive means. In addition, fastening means 145 may allow to control a separation between applicator heads 110. The shape and/or size of fastening means 145 may be used to this end.

The fastening means 145 or connections between the various applicator heads may be formed as hinges, allowing one applicator head to rotate with respect to another.

FIG. 4 also shows that each applicator head may include a flexible tube 150 through which each applicator head may be connected to a non-illustrated control unit (base station). The control unit may include e.g. a pump for applying vacuum, a power supply, e.g. connection with the electrical grid, and an RF generator. Optionally, the control unit may include a cooling system which may be used to cool the cavity 115 in case that overheating is detected.

In an example, the RF generator may be a sinusoidal RF generator. Other waveforms, e.g. squared and triangular may be used. The frequency of the RF generator may be in a range of 100 kHz to 3 MHz, and specifically in a range of 0.5 to 2 MHz. The power of the RF generator may be in a range of 0 to 200 W, and specifically in a range of 50 to 150 W. The flexible tube can provide electric, electronic and pneumatic connection between the control unit and the applicator head.

FIG. 5 schematically represents an example of a side view of an applicator head 110. This side view corresponds to a side view of a shorter side of e.g. the applicator head 110 of FIG. 1 or 2. In an example, a shorter side of an applicator head 110 may have a length of around 10 cm.

Figure 6:
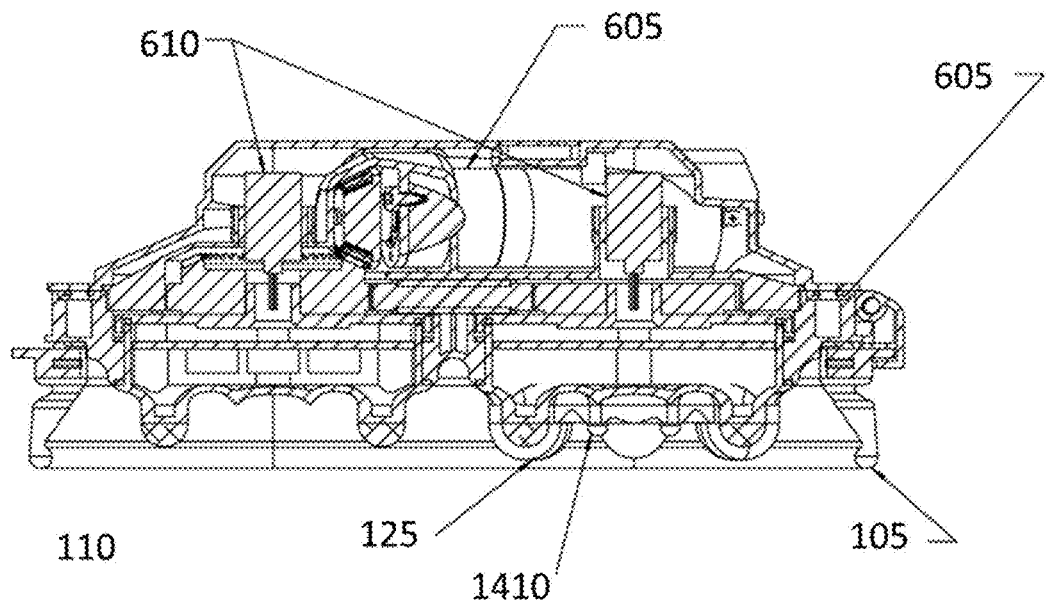
FIG. 6 schematically illustrates the interior of the applicator head of the example of FIG. 5 along line C-C.

The interior of the applicator head 110 of the example of FIG. 5 along line C-C may be seen in FIG. 6. In an example, the longer side of an applicator head 110 may have a length in a range of 15 to 20 cm. In this example, the electrodes are also convex and circular. Applicator head 110 includes a motor 605 to drive the electrode supports and/or the electrodes. Applicator head 110 may also include an electrical collector 610 in order to continuously transmit electrical energy to one or more electrode supports 120, e.g. rotatable electrode supports. In addition, the applicator head 110 comprises a lip 105 and a perimetral sealing gasket 615 in this example. Furthermore, an applicator head 110 may optionally include a skin temperature sensor 1410 in some examples.

The apparatus described herein may be used to perform an effective and safe method for treating a skin of a subject in an automatic way, i.e. without an operator holding and/or moving an apparatus head 110. Such a method is described in FIG. 7.

Figure 7:
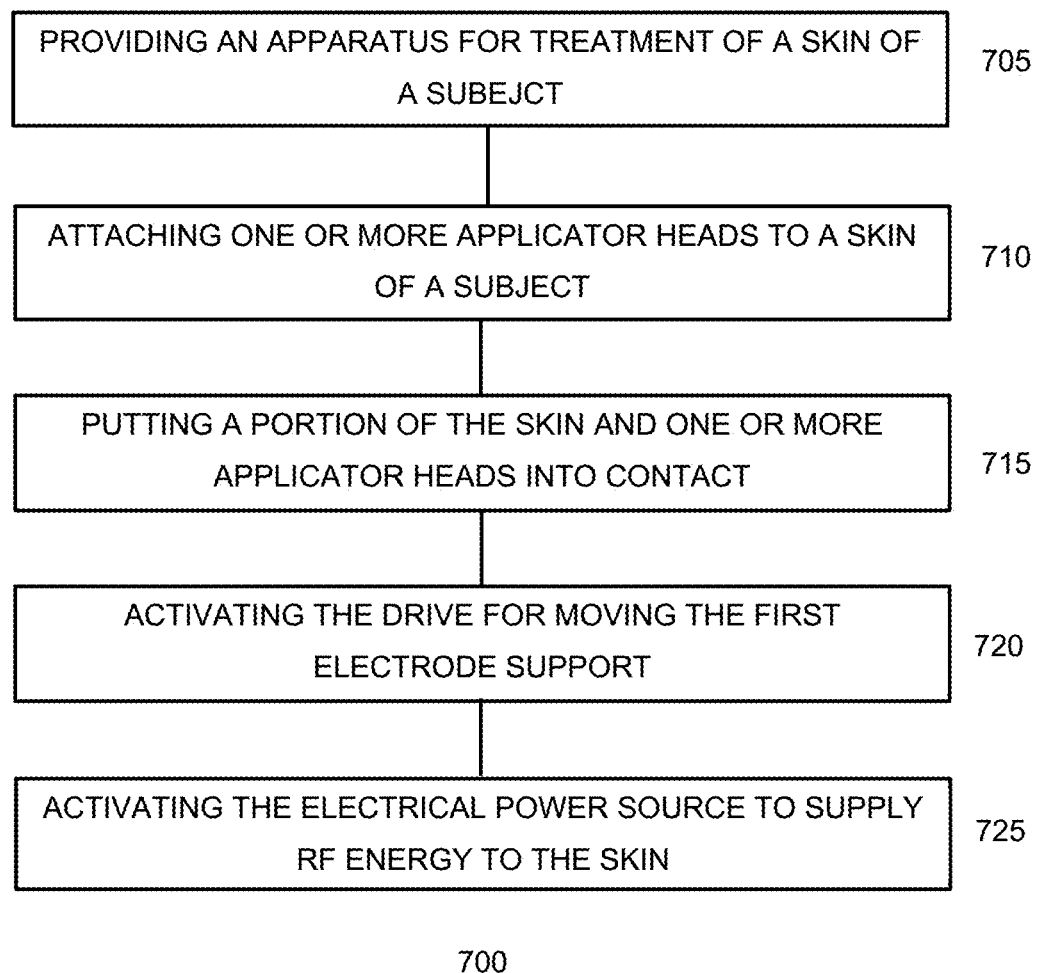
FIG. 7 is a flow chart of a method for treating a skin of a subject.

FIG. 7 illustrates a flowchart of a method 700 for treating a skin of a subject. The method 700 comprises, at step 705, providing an apparatus for treatment of a skin of a subject as disclosed herein. The apparatus may include one or more applicator heads 110, which may be any of the one or more applicator heads 110 mentioned throughout this disclosure, e.g. with respect to any of FIGS. 1-6.

Then, method 700 comprises, at step 710, attaching one or more applicator heads 110 to a skin of the subject. In some examples, the attachment of one or more applicator heads 110 to the skin of the subject may be performed through at least one of: suction and one or more mechanical fasteners, e.g. straps. As indicated above, fixing means enable one or more applicator heads 110 to be attached to the skin of a subject during the entire RF treatment. Suction of a skin may comprise applying vacuum. A sealing lip may be incorporated to an applicator head 110 to facilitate suction and/or vacuum application.

The method 700 further comprises, at block 715, putting a portion of the skin and one or more applicator heads 110 into contact. This shall be interpreted as putting at least the first 125 and second 130 electrodes in contact with the skin. This step may be performed substantially simultaneously to attaching one or more applicator heads 110 to the skin of the subject or afterwards, depending on the fixing means 105 used. For instance, in examples where suction is used, attaching an applicator head 110 to the skin and putting a portion of the skin and the applicator head 110 into contact, e.g. by introducing a portion of skin into a cavity 115 of the applicator head 110, may be substantially done at the same time. In other examples where suction is not used as fixing means 105, the attachment, e.g. through straps, of an applicator head 110 to the skin is performed before putting a portion of the skin and the applicator head 110 into contact. In general, suction could be used to facilitate the introduction of the portion of the skin into the cavity 115.

Once one or more applicator heads 110 are attached to a skin of a subject and a portion of a skin of a subject is in contact with one or more applicator heads 110, method 700 further includes, at block 720, activating the drive for moving the first electrode support. Thus, at least the first electrode support 120 comprising at least a first electrode 125 is moved such that a distance between the first electrode 125 and a second electrode 130 is varied.

The method 700 also comprises, at block 725, activating the electrical power source to supply RF energy to the skin. Thus, radio frequency, RF, energy may be applied to the skin with at least the first electrode 125.

In general, applying radio frequency, RF, energy to the skin with at least the first electrode 125 is not performed until the electrodes have started to move. This is due to security reasons, as this enables to check that the electrodes are in an appropriate contact with the skin to be treated.

If suction is used, suction may also be performed before applying RF energy. This ensures that contact between the electrodes and the skin is maintained, and arcing and sparking from the electrodes may be reduced. In some examples, suction is around 50 mbar. In some other examples, suction is around 500 mbar. A check that a suitable level of suction has been attained may be performed by a pressure sensor included in the corresponding applicator head 110. In some examples, when a pressure sensor detects a certain pressure value, the application of RF energy begins.

Optionally, as an additional security measure, RF energy may be applied through the electrodes in order to check that the electrodes are in contact with the skin. Additionally or alternatively, an impedance meter may be used to perform the check. Once a return signal and/or a certain impedance value, e.g. included in a range of values, have been detected, RF energy will start to be applied through the electrode(s).

Additionally, method 700 may optionally include joining a first and at least a second applicator heads, e.g. through fasteners or fastening means 145. This step may be carried out before the attachment of one or more applicator heads 110 to the skin of the subject. For instance, several applicator heads 110 may be joined to one another through male and female connectors and then the applicator heads 110 may be attached to e.g. a thigh.

The use of more than one or two applicator heads 110 and/or joining two or more applicator heads 110 offers a larger treatment area with respect to usually performed RF treatments, wherein an operator needs to hold and/or move an applicator head along the subject's skin. As an operator has only two hands, the regions to be treated are limited. However, the use of two or more applicator heads 110 as described herein enables to treat more regions at the same time, while the regions would be continuously receiving RF energy as the moving electrodes would be continuously covering these regions.

The electrodes may move in any direction with respect to the applicator head 110 including them. For instance, they may move linearly and/or circularly.

Figure 8:
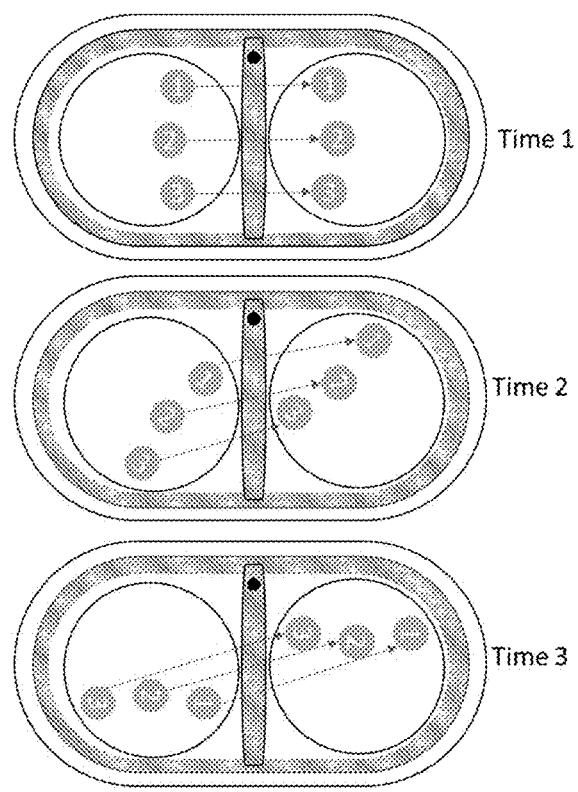
FIG. 8 schematically illustrates an example of the movement of the electrodes of an applicator head with time.

FIG. 8 schematically illustrates an example of the movement of the electrodes of the applicator head 110 of FIG. 2 with time. At a time 1, the electrodes of each electrode support 120 are substantially facing each other. At a time 2 and at a time 3 the electrodes of each plate have rotated clockwise and the distance between the electrodes included in the electrode supports 120 has been changed. In some other examples, the rotation of the electrodes may be additionally or alternatively be counterclockwise.

In FIG. 8, the two electrode supports 120 move at the same rotational speed. This enables performing a more homogenous RF treatment. However, in other examples, one or more electrodes and/or one or more electrode supports may move at different speeds. For instance, two electrode supports 120 may move at a different rotational speed. This may be useful when a region to be treated, e.g. due to specific features of the tissue, may benefit from a faster RF energy application than another region.

The RF treatment 500 may include monopolar, bipolar and/or multipolar operation during the same treatment.

In monopolar operation, the second electrode 130 is a passive electrode which, previously to applying RF energy through at least the first electrode 125, has been placed on the skin of the subject. During monopolar operation, the generated heat density between the first 125 and the second 130 electrodes continuously moves due to at least the movement of the first electrode 125. Accordingly, this reduces the possibility of overheating tissue and skin damage, e.g. skin burn, may be minimized.

In bipolar operation, the second electrode 130 has an opposite polarity from the first electrode 125 polarity and the first 125 and second 130 electrodes form a first pair of electrodes. RF energy is applied to the skin through at least the first pair of electrodes.

In the example of FIG. 8, electrode 1 in the left electrode support 120 may be the first electrode 125 and electrode 1 in the right electrode support 120 may be the second electrode 130. RF energy may be applied through this electrode pair. In addition, electrodes 2 in each electrode support 120 may form a second pair of electrodes and RF energy may be applied through this pair of electrodes too. The same may apply to electrodes 3. Therefore, FIG. 6 may represent a tripolar arrangement.

Figure 9A:
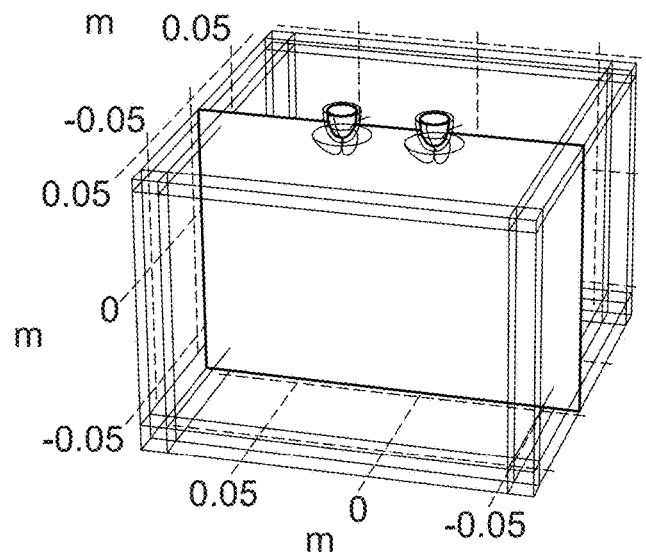
FIGS. 9A and 9B illustrate the effect of distance between electrodes in a particular example.
Figure 9B:
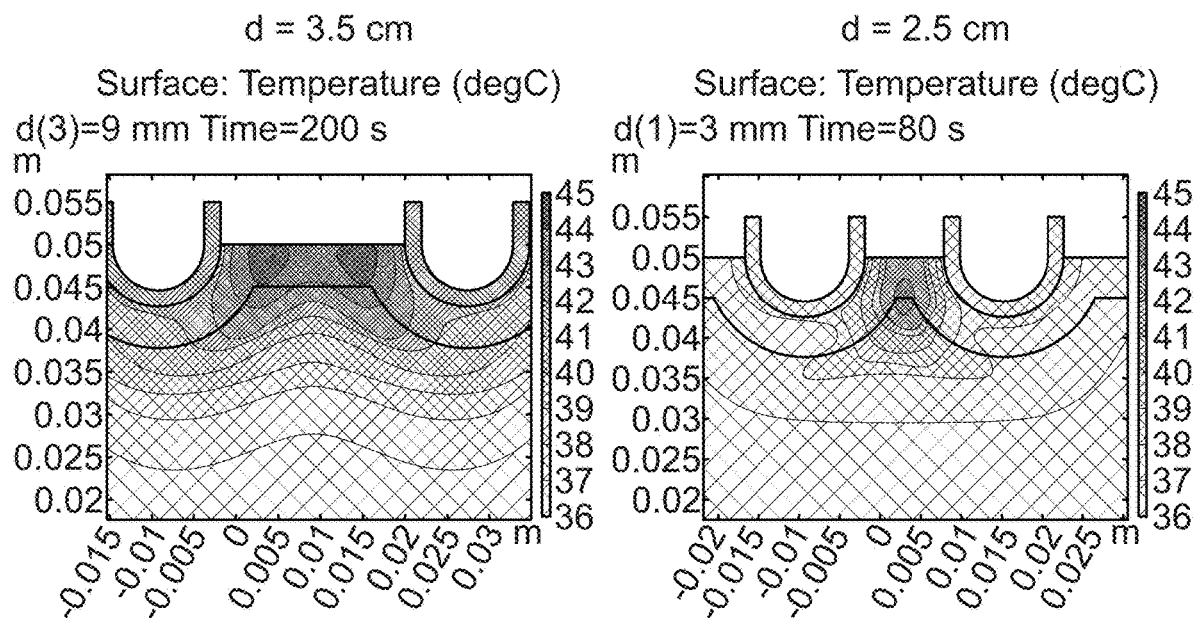

FIGS. 9A and 9B illustrate an example of the effect of the distance between two electrodes when applying an RF treatment. In the simulations of this example, both electrodes have a diameter of 15 mm, and a power of 50 W and a frequency of 0.1 MHz have been applied.

FIG. 9A shows two electrodes, e.g. capacitive electrodes, in contact with a skin of a subject. FIG. 9B shows the temperature distribution created in the transversal cut indicated in FIG. 9A for two distances d between the pair of electrodes in FIG. 9A operating in a bipolar mode (d=3.5 cm in the left image and d=2.5 cm in the right image). The temperature distribution in the left image corresponds to a time of t=200 s after starting the application of RF energy and the temperature distribution in the right image corresponds to a time of t=80 s after the start of the application of RF energy.

Figure 10:
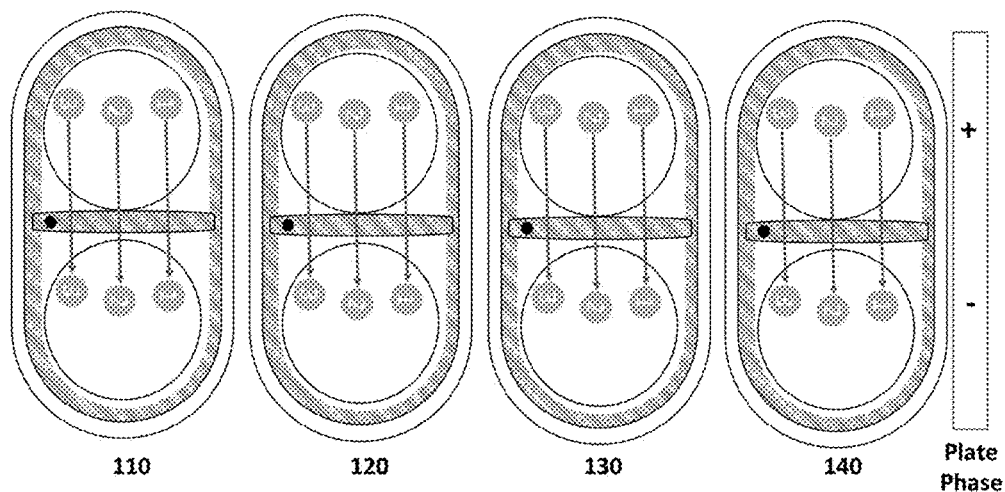
FIG. 10 schematically illustrates an example configuration of the polarity during a method for treating a skin of a subject.
Figure 11:
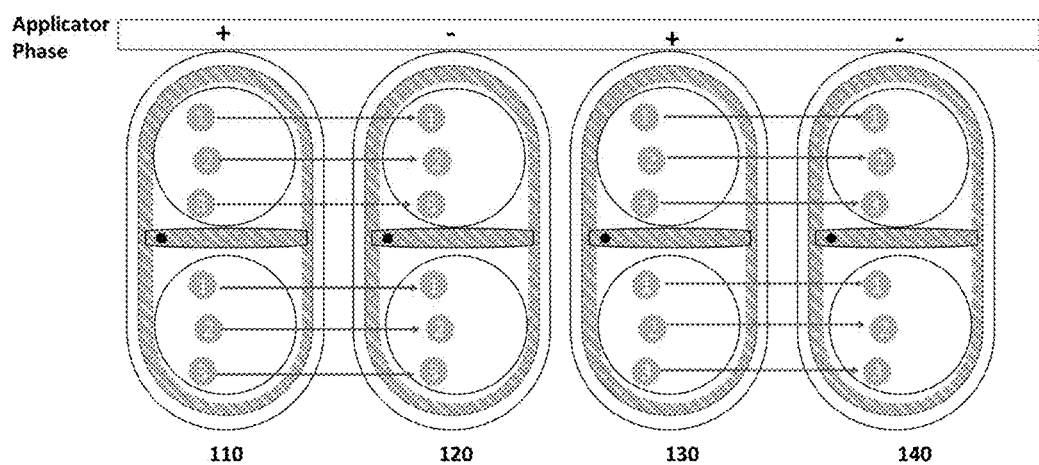
FIG. 11 schematically illustrates another example configuration of the polarity during a method for treating a skin of a subject.

The left image shows that, at d=3.5 cm, a critical temperature (i.e., a temperature at which a skin burn may occur, e.g. above 43° C.) has been attained at t=200 s. Therefore, sufficient time has passed to attain a substantially homogeneous temperature in the tissue between the electrodes. In contrast, the right image shows that, at d=2.5 cm, the critical temperature has been reached already at t=80 s. A substantially homogeneous temperature has not been attained in the tissue between the two electrodes. Thus, in the left image, more tissue has been heated, in particular in a homogenous way, and heat has also reached bigger depths in the tissue. As already explained before, continuously changing distances between the electrodes can provide homogenous and effective treatment of an area of tissue.

Where RF energy is applied through a pair of electrodes, each electrode of the pair may be located in the same applicator head 110, such as in FIG. 8 or 10, or in different applicator heads, such as in FIG. 11.

Figure 12:
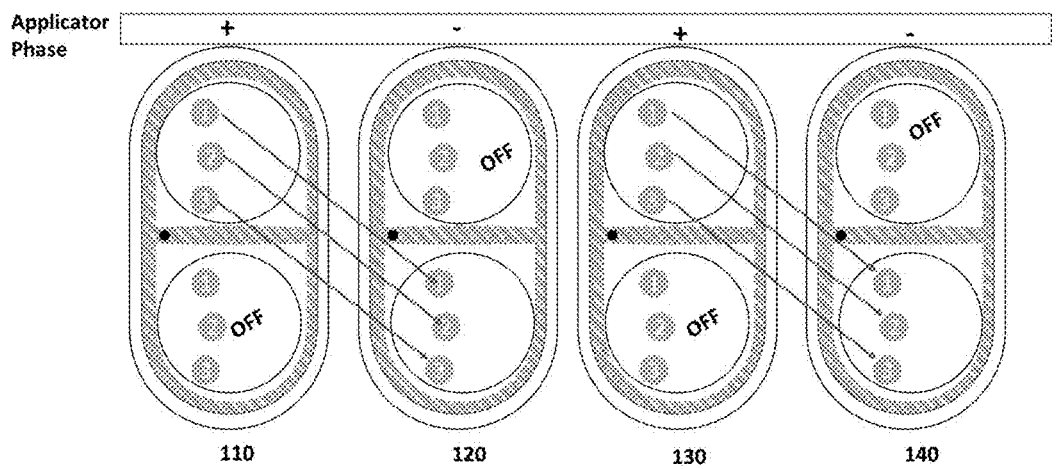
FIG. 12 schematically illustrates an example of a method for treating a skin of a subject with the polarity configuration of FIG. 9 wherein not all the electrodes are simultaneously used to deliver RF energy.

FIGS. 10, 11 and 12 illustrate example configurations of the polarity during a method for treating a skin of a subject. The arrows show the direction of the current flow between the corresponding electrode pairs for the illustrated polarity. Four applicator heads like the applicator head 110 of FIG. 2 are positioned next to each other such that two rows of electrode supports 120 can be distinguished, namely an upper row and a lower row. In these examples, all the electrodes included in a support electrode 120 have the same polarity. For instance, all the electrodes included in an electrode support 120 may have a positive polarity.

In FIG. 10, the electrode supports 120 of the upper row have a positive polarity and the electrode supports 120 of the lower row have a negative polarity. The electrode pairs 1, 2, 3 in each applicator head 110 operate in a bipolar mode and e.g. current flows from electrodes 1 in the upper row to electrodes 1 in the lower row. At a different time, the polarities of the upper and lower row may be inverted. This example of polarity configuration enables to heat tissue comprised between the electrode supports 120 of the same applicator head 110.

In FIG. 11, alternating applicator heads 110 have different polarities. In bipolar operation with this polarity configuration, current may flow between electrodes in contiguous applicator heads 110, in particular between the same row. Thus, in FIG. 9, tissue comprised between applicator heads 110 may be heated.

FIG. 12 illustrates another possibility to heat tissue between applicator heads 110. In this example, the polarity configuration of FIG. 9 is applied, but RF energy is not applied through all the available electrodes. In particular, RF energy is not applied through the electrodes of electrode supports 120 in alternate applicator heads 110 and alternating rows. This enables to heat tissue comprised between applicator heads 110 and between different rows.

The concepts in FIGS. 10-12 may combined during the same RF treatment. Polarity between applicator heads 110 and/or electrode supports 120 may be changed such that tissue between electrode supports 120 included in same or different applicator heads 120 is heated.

Figure 13:
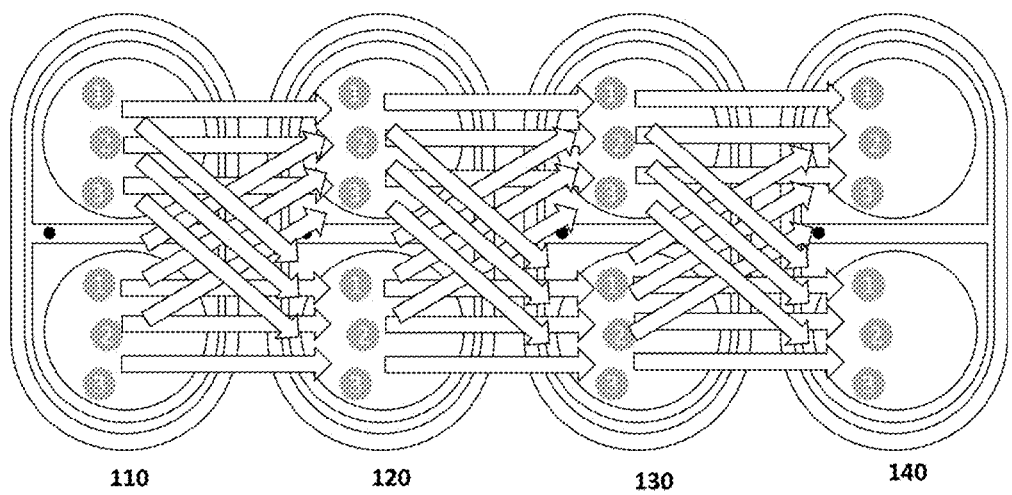
FIG. 13 schematically illustrates the treated regions in an example of a method for treating a skin of a subject which combines examples of FIGS. 8-10.

An example illustrating this combination is shown in FIG. 13. In the example of FIG. 11, the polarity configurations illustrated may be applied in order. For instance, in an example, the configuration of FIG. 8 may be applied before the configuration of FIG. 10. In the same or another example, the configuration of FIG. 10 may be applied before the configuration of FIG. 8. Accordingly, not all the electrodes may be used for applying RF energy to the tissue during an RF treatment. Some of the electrodes may not be used when the RF treatment is initiated and/or some electrodes may stopped being used during the RF treatment.

Figure 14:
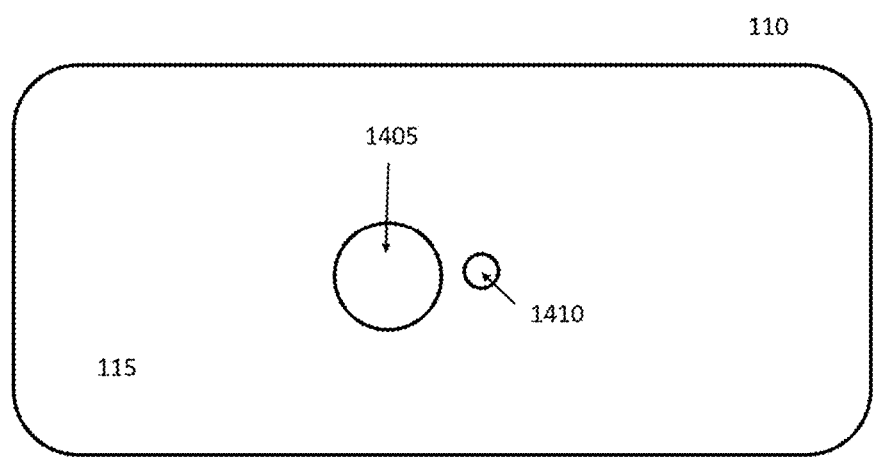
FIGS. 14, 15 and 18 schematically illustrate an applicator head according to various examples.

FIG. 14 schematically illustrates another applicator head 110 according to an example. In this example, the applicator head 110 comprises an electrode support 120 comprising an RF electrode 1405 and a skin temperature sensor 1410. The electrode support 120 is movably mounted with respect to a base of the applicator head 110. The skin temperature sensor 1410 may be included in the electrode support 120 or may be included in a different support. In any case, the electrode 1405 and the skin temperature sensor 1410 are configured to move together with respect to a skin of a subject. Although the applicator head 110 has a rectangular shape and the electrode 1405 and skin temperature sensor 1410 have circular shapes, other shapes are possible. In some examples, the applicator head 110 may have a circular or squared shape. In these or another examples, the electrode 1405 and/or the skin temperature sensor 1410 may have a squared shape with rounded corners.

The applicator head 110 may be connected, e.g. mechanically and electrically, to a control unit (not shown). The control unit controls RF energy applied through the electrode 1405.

Incorporating a skin temperature sensor 1410 which is jointly movable with an electrode 1405 makes it possible to measure an average temperature of the skin covered by the electrode 1405 and the skin temperature sensor 1410 when moving. In addition, there is no interference between the energy and/or temperature of the electrode 1405 and the skin temperature measurements performed by the skin temperature sensor 1410. Accordingly, the RF energy applied through the electrode 1405 may be controlled and adjusted by a control system based on an average temperature of the skin being treated.

A control system may be included in a control unit. A control system may include a processor and a memory. The control system receives measurements from one or more skin temperature sensors.

A distance between an electrode 1405 and a skin temperature sensor 1410 may be between 0.5 mm and 20 mm, and specifically between 2 and 15 mm.

Figure 15:
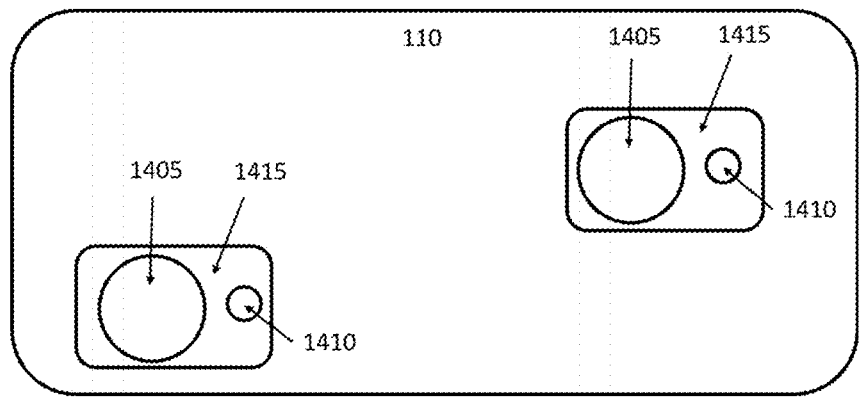

FIG. 15 illustrates an applicator head 110 according to another example. Herein, an electrode 1405 and a skin temperature sensor 1410 are included in the same electrode support 120, which may be also called an electrode and skin temperature sensor support 1415. The electrode and skin temperature sensor support 1415 makes it possible to easily move at least an electrode 1405 and a skin temperature sensor 1410 together.

Figure 16:
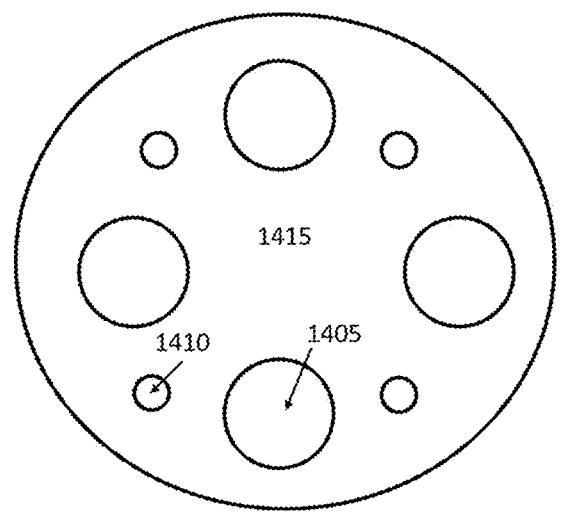
FIGS. 16 and 17 schematically illustrate different examples of an electrode support.

FIG. 16 shows an electrode and skin temperature sensor support 1415. In this example, the electrode and skin temperature sensor support 1415 is circular and includes four electrodes 1405 and four skin temperature sensors 1410. A skin temperature sensor 1410 is adjacent to two electrodes 1405 in this example. Placing a skin temperature sensor 1410 adjacent to more than one electrode 1405 makes it possible to consider the contributions to the skin temperature of the two or more electrodes 1405.

Figure 17:
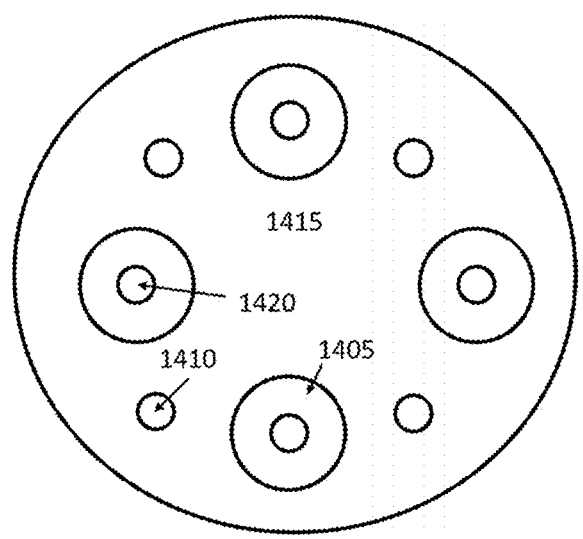

FIG. 17 illustrates the electrode and skin temperature sensor support 1415 of FIG. 16, this time the electrodes 1405 including an electrode temperature sensor 1420 in contact with each electrode 1405. In some other examples, not all the electrodes 1405 include an electrode temperature sensor 1420. As indicated by its name, an electrode temperature sensor 1420 measures the temperature of the electrode 1405 that the electrode temperature sensor 1420 is in contact with. This may be used as a security measure. For instance, if an electrode temperature is too high, e.g. higher than a threshold, power and/or frequency for an RF treatment may be decreased.

In some examples, the electrode temperature sensor 1420 is in contact with an interior of an electrode 1405 only. An interior of an electrode may be considered the part of an electrode 1405 that is configured not to be in contact with a skin of a subject. And an exterior of an electrode 1405 may be considered the part of an electrode 1405 which is configured to be in contact with the skin of the subject. Thus, placing the electrode temperature sensor 1420 in contact with an interior of an electrode 1405 enables measuring the temperature of the electrode 1405 while minimizing the influence of the skin temperature on said measurement.

Figure 18:
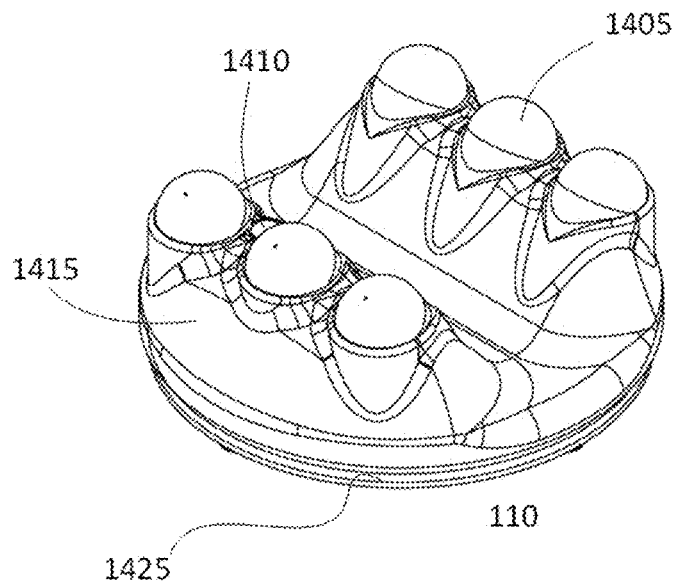

FIG. 18 illustrates another example of an applicator head 110. Applicator head 110 comprises a base 1425 at which the applicator head may be connected to a tube or tubular extension with the base station. The base 1425 may include a motor and an actuator or drive for rotating the electrode and skin temperature support 1415, which is rotatably mounted to the base 1425.

In this example, the applicator head 110 includes six electrodes 1405 placed in two rows, each row having three electrodes 1405, and one skin temperature sensor 1410 adjacent to two electrodes 1405. In another example, an applicator head 110 may include two electrode 1405 rows, each row having four electrodes 1405, and one skin temperature sensor 1410 comprised in one of the rows adjacent to two electrodes 1405, e.g. adjacent to the two central electrodes.

Figure 19:
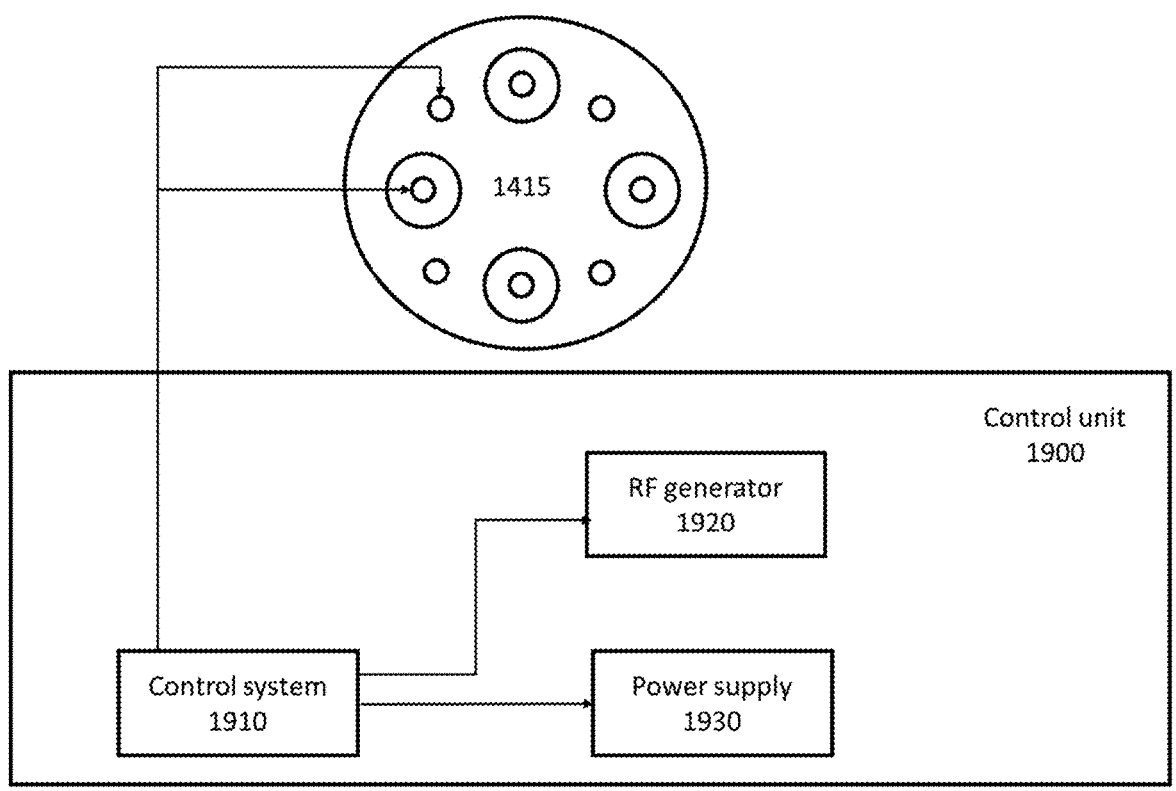
FIG. 19 schematically illustrates how a skin temperature sensor and/or an electrode temperature sensor may be connected to a control unit.

FIG. 19 schematically illustrates how skin temperature sensors 1410 and/or electrode temperature sensors 1420 are in contact with the control system of a control unit 1900 according to an example. The control system 1910 receives measurements from one or more temperature sensors 1410, 1420 and, if necessary, instructs an RF generator 1920 and/or a power supply 1930 to modify e.g. power and/or frequency.

In particular, a control may include e.g. a PID control to reach and maintain a temperature of a skin that is close to a reference temperature. A control may further include security measures, such as an interruption of a treatment if a maximum temperature is reached. It may further include detection of a possible malfunction (e.g. of a specific electrode) and a reaction to that malfunction.

The features of the applicator header 110 described through FIGS. 14 to 17 may also include any of the features described in relation to the applicator head 110 described in relation with FIGS. 1 to 6. For instance, an apparatus 100 may include an applicator head 110 which may comprise a first electrode 125 and a second electrode 130, the first electrode 125 being configured to be movable such that a distance between the first electrode 125 and the second electrode 130 is varied. The applicator head 110 may further include one or more skin temperature sensors 1410 adjacent to the first and/or second electrodes 125, 130; one or more skin temperature sensors 1410 being movable together with the electrode(s) which to they are adjacent to. The apparatus 100 may also include fixing means 105 to attach the applicator head 110 to the body of the subject.

In some other examples, one or more electrodes 125, 130 included in the applicator head 110 may comprise an electrode temperature sensor 1420, in particular in contact with an interior of an electrode. Still in some other examples, the apparatus 100 may include more than one applicator head 110, one or more applicator heads 110 including one or more features described throughout this disclosure.

Combining aspects from the applicator heads 110 described in FIGS. 1 to 6 with aspects from the applicator heads 110 described in FIGS. 14-18 may be beneficial. For instance, an electrode 1405 may be movable with respect to the other electrode 1405 in FIG. 15. This embodiment incorporates the advantages derived from varying a distance between two electrodes and the advantages derived from having a skin temperature sensor 1410 adjacent to an electrode 1405.

Figure 20:
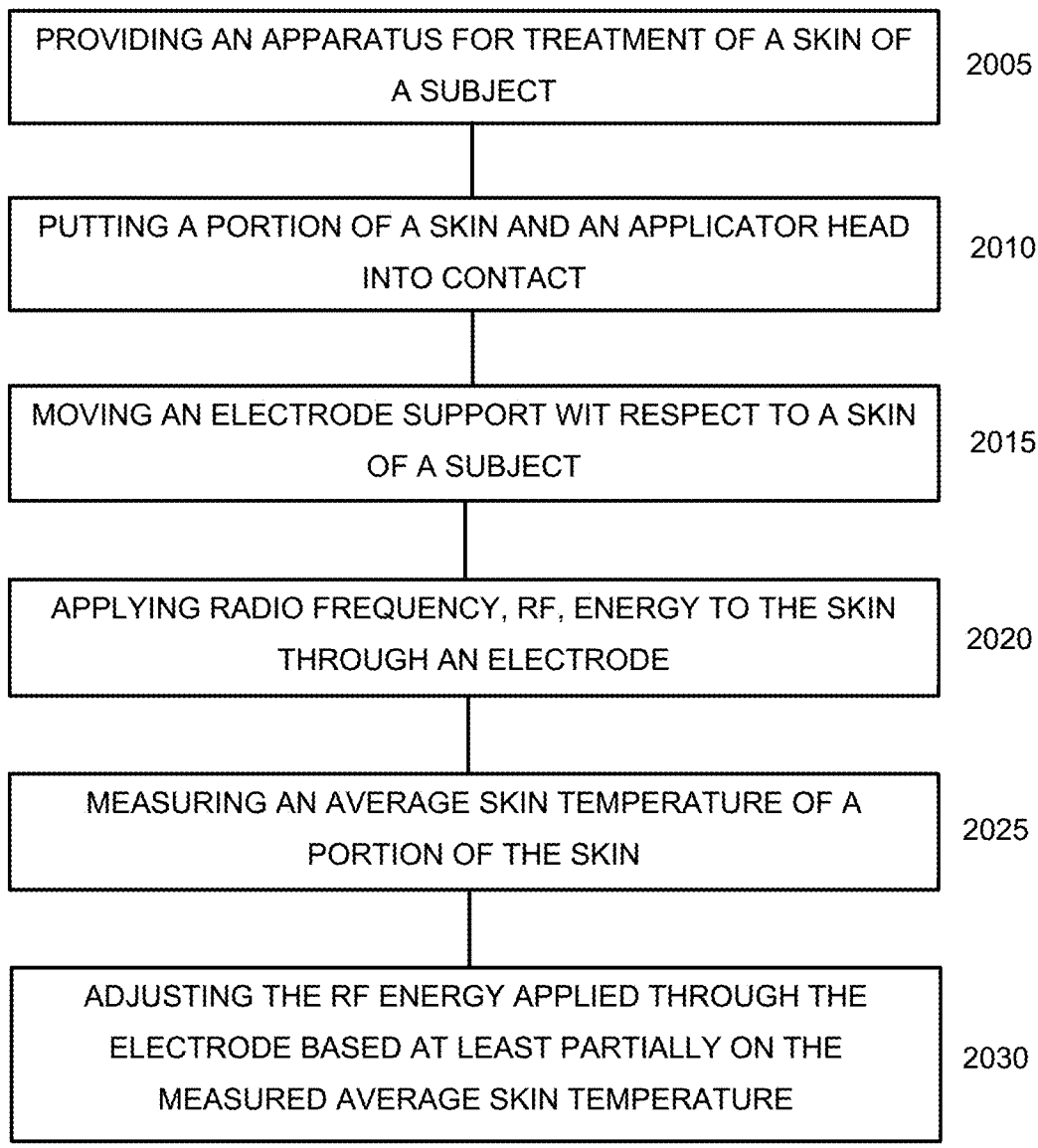
FIG. 20 is a flow chart of another method for treating a skin of a subject

FIG. 20 illustrates a flowchart of a method 2000 for treating a skin of a subject. Method 2000 includes a block 2005 of providing an apparatus for treatment of a skin of a subject as disclosed herein. The apparatus may comprise one or more applicator heads 110 such as the ones disclosed in FIGS. 14-18, i.e. including an electrode 1405 and a skin temperature sensor 1410 that may be movably together, e.g. by an electrode and skin temperature sensor support 1415.

Method 2000 further comprises, at block 2010, putting a portion of the skin and an applicator head 110 into contact. This may mean simply placing an applicator head on a portion of skin, and thereby putting a portion of the skin into contact with at least an electrode and a skin temperature sensor adjacent to the electrode.

This step may be performed e.g. by applying suction through a suction recess included in the applicator header 110 such that a portion of the skin is sucked into a cavity of the applicator head 110, in the examples of applicator heads having a cavity. In general, the explanations related to suction for introducing a portion of the skin into an applicator head 110 and the possibilities for checking that the electrodes 1405 are in contact with the skin provided with regard to FIG. 7 also apply to block 2010 of FIG. 20. Pressing the applicator head 110 against the skin, e.g. by a physician, may also serve to put the applicator head 110 into contact with the skin. Fasteners or fastening means may also be used for this purpose. This aspects may be combined among them.

Method 2000 also comprises a block 2015 of moving an electrode support 120 with respect to a skin of the subject. This may facilitate moving an electrode 1405 and a skin temperature sensor 1410 adjacent to the electrode 1405 in a joint manner with respect to the skin of the subject. The electrode support 120 includes at least one electrode and may also include a skin temperature sensor 1410. In some examples, this movement may be circular. Moving an electrode support 120 is performed after the skin has been put into contact with the applicator head 110.

Method 2000 further comprises a block 2020 of applying RF energy to the skin through an electrode 1405. In general, this step is performed once the electrode has started to move, as explained with regard to FIG. 7. The possibility of applying RF energy before starting the movement of one or more electrode(s) is however not excluded.

Afterwards, when the electrode 1405 and the skin temperature sensor 1410 adjacent to the electrode 1405 are moving, method 2000 includes a block 2025 of measuring an average skin temperature of a portion of the skin. Such a portion of the skin may be delimited by the movement performed by the electrode 1405 and the skin temperature sensor 1410.

Finally, after an average skin temperature has been measured, method 2000 further comprises a block 2030 of adjusting the RF energy applied through the electrode 1405 based on the measured average skin temperature. Such an adjustment may be performed by a control system connected to the applicator head 110.

This method enables a better control and adjustment of the RF energy applied through the electrode(s) 1405 during the RF treatment. This facilitates keeping a constant and homogeneous skin temperature throughout the treated skin while avoiding injuries, e.g. skin burn. For example, if an operator is holding an applicator head 110 and leaves it on the skin of the subject possibly causing inadvertent skin burn, the control system may, based on an average skin temperature measurement, decrease the RF energy applied through some electrodes 1405 in order to avoid or reduce skin damage.

The adjusting may also include keeping a current level of RF energy. For instance, if a measured average skin temperature is compared to a desired average skin temperature and these values are substantially coincident, the adjustment consists in maintaining the current RF energy.

In some examples, method 2000 may further comprise programming a reference average skin temperature, e.g. by an operator, and adjusting, by the control system, the RF energy applied through the electrode 1405 based on a measured average skin temperature to keep the reference average skin temperature.

Accordingly, both an effective and safe RF treatment may be performed. In some examples, the reference average skin temperature may be between 40° C. and 50° C. In an example, the reference average skin temperature is 43° C. When a measured average skin temperature deviates from 43° C., the control system may adjust the RF energy applied through some electrodes. In this or other examples, adjusting the RF energy may include adjusting at least one of: power and frequency. For instance, in the previous example, if a measured average skin temperature is of 41° C., the control system may increase the power in order to increase the skin temperature to 43° C.

In some examples, the reference average skin temperature is the same for all the electrodes 1405. In some other examples, a group of electrodes 1405, e.g. electrodes 1405 sharing a same electrode and skin temperature sensor support 1415, may have a different reference average skin temperature than other electrodes 1405, e.g. electrodes 1405 sharing another electrode and skin temperature sensor support 1415. This may help to deliver a homogeneous RF treatment to tissue regions having different RF energy needs.

If more than one applicator head 110 is used, different applicator heads 110 may have the same or different reference average skin temperatures.

In some examples, the electrode 1405 and the skin temperature sensor 1410 perform a rotational movement. This enables to apply RF energy to a greater extension of skin than when using a linear movement, and also in a more homogeneous way. In some of these examples, the rotational speed of the electrode and the skin temperature sensor may be in a range of 1 to 100 rpm.

If an electrode 1405 includes an electrode temperature sensor 1420, method 1800 may further include measuring the temperature of an electrode 1405 by an electrode temperature sensor 1420; and when the measured electrode temperature exceeds an electrode temperature threshold: at least decreasing the energy applied through the electrode 1405 and/or interrupting the energy applied through the electrode 1405.

As a security measure, an electrode temperature threshold may be programmed by an operator such that, when exceeded, RF energy applied through the electrode 1405 is decreased and/or stopped. In some other examples, an electrode temperature threshold is fixed by a manufacturer and may not be modified by an operator.

In some examples, an electrode temperature threshold may be between 40 and 50° C. In an example, the electrode temperature threshold is 47° C. A measured electrode temperature is 48° C. Therefore, RF energy is decreased, e.g. by diminishing the power supplied to the electrode. If a subsequent electrode temperature measurement is still over 47° C., RF energy may be reduced again, or RF may be interrupted (e.g. power supply may be stopped).

Aspects of method 2000 and method 700 may be combined. For instance, method 2000 may further include attaching an applicator head to a skin of the subject and moving a first electrode and a skin temperature sensor adjacent to the first electrode such that a distance between the first electrode and a second electrode is varied.

This combination enables again to obtain a method including the advantages related to varying a distance between electrodes and the advantages related to including a skin temperature sensor adjacent to a movable electrode commented above. In particular, the efficiency and safety of an RF treatment are further enhanced.

An RF treatment according to any of the methods described herein may last in a range of 10 to 60 minutes. In some examples, the duration of an RF treatment is indicated to a control system by an operator.

During any of the method described herein, RF energy may be applied through a single electrode and/or through a pair of electrodes including two electrodes of opposite polarity. I.e., monopolar, bipolar and/or multipolar operation may be alternated during any of these RF treatments.

For reasons of completeness, various aspects of the present disclosure are set out in the following numbered clauses:

Clause 1. An applicator head for use in an apparatus for treatment of a skin of a subject, the applicator head comprising:
an electrode support comprising a radio frequency, RF, electrode and a skin temperature sensor adjacent to the electrode;
wherein the electrode support is movably mounted with respect to a base of the applicator head.

Clause 2. The applicator head of clause 1, wherein the applicator head further comprises at least an additional electrode and the skin temperature sensor is also adjacent to at least the additional electrode.

Clause 3. The applicator head of any of clauses 1-2, the applicator head further including at least an additional skin temperature sensor adjacent to one or more of the electrodes.

Clause 4. The applicator head of any of clauses 1-3, wherein a distance between the electrode and the skin temperature sensor is in a range of 0.5 mm to 20 mm, and specifically in a range of 2-10 mm.

Clause 5. The applicator head of any of clauses 1-4, the applicator head further comprising an electrode temperature sensor in contact with one of the electrodes.

Clause 6. The applicator head of any of clauses 1-5, further comprising a cavity for receiving a portion of a skin of the subject, and in particular further comprising a suction orifice configured to be coupled to a pump for sucking air through the suction orifice.

Clause 7. The applicator head of clause 6, further comprising a flexible lip arranged along a border of the cavity for sealing the cavity.

Clause 8. The applicator head of any of clauses 1-7, further comprising one or more mechanical fasteners to fix the applicator head to the skin.

Clause 9. The applicator head of clause 8, wherein the fasteners include one or more straps.

Clause 10. The applicator head of any of clauses 1-9, wherein at least a first electrode having a skin temperature sensor adjacent to the first electrode is movable such that a distance between the first electrode and a second electrode is varied.

Clause 11. The applicator head of any of clauses 1-10, further comprising a drive for rotating the electrode support.

Clause 12. An apparatus for treatment of a skin of a subject comprising
one or more applicator heads according to any of clauses 1-11;
an electric power source and a control system for controlling electrical energy supplied to at least one of the RF electrodes.

Clause 13. A method for treating a skin of a subject comprising:
providing the apparatus of clause 12;
putting a portion of the skin and an applicator head into contact;
moving the electrode support with respect to a skin of the subject;
applying radio frequency, RF, energy to the skin through one or more of the electrodes;
measuring an average skin temperature of a portion of the skin; and
adjusting the RF energy applied through the one or more electrodes based at least partially on the measured average skin temperature.

Clause 14. The method of clause 13, further comprising:
determining a reference average skin temperature, specifically wherein the reference average skin temperature is in a range of 40 to 50° C.; and
adjusting, by a control system, the RF energy applied through the electrodes based on a measured average skin temperature to maintain the average skin temperature close to the reference average skin temperature.

Clause 15. The method of any of clauses 13 or 14, wherein the adjusting the RF energy includes adjusting at least one of: power and frequency.

Clause 16. The method of any of clauses 13-15, wherein one or more of the electrodes and the skin temperature sensor perform a rotational movement.

Clause 17. The method of clause 16, wherein the rotational speed of the electrode and the skin temperature sensor is 5 to 100 rpm, specifically 10 to 60 rpm.

Clause 18. The method of any of clauses 13-17, further comprising:
measuring the temperature of an electrode with an electrode temperature sensor; and
when the measured electrode temperature exceeds an electrode temperature threshold: decreasing the energy applied through the electrode and/or interrupting the energy applied to the electrode.

Clause 19. The method of clause 18, wherein the electrode temperature threshold is in a range of 40° C. to 50° C.

Clause 20. The method of any of clauses 13-19, further comprising:
attaching an applicator head to a skin of the subject;
moving a first electrode and a skin temperature sensor adjacent to the first electrode such that a distance between the first electrode and a second electrode is varied.

Clause 21. The method of any of clauses 13-20, wherein RF energy is applied through a single electrode or through a pair of electrodes including two electrodes of opposite polarity.

Clause 22. The method of any of clauses 13-21, wherein an RF treatment time ranges from 10 minutes to 60 minutes.

Clause 23. An applicator head for use with an apparatus for treatment of a skin of a subject, the applicator head configured for being fixed to the skin of the subject comprising:
a first radio frequency, RF, electrode, mounted on a first electrode support, wherein the first electrode support is movable with respect to a base of the applicator head such that a distance between the first electrode and a second electrode is varied in use.

Clause 24. The applicator head of clause 23, wherein the applicator head further comprises the second RF electrode.

Clause 25. The applicator head of any of clauses 23-24, wherein both the first and second RF electrodes are movable with respect to the base of the applicator head.

Clause 26. The applicator head of clause 24, wherein the first RF electrode is mounted on the first electrode support, and the second RF electrode is mounted on a second electrode support, and wherein the first and the second electrode supports are movable with respect to the base of the applicator head.

Clause 27. The applicator head of clause 26, wherein the first electrode support is operatively connected to the second electrode support.

Clause 28. The applicator head of clause 27, wherein the first electrode is eccentrically mounted on the first electrode support.

Clause 29. The applicator head of any of clauses 26-28, wherein the first electrode support includes a first plurality of RF electrodes, and the second electrode support includes a second plurality of RF electrodes.

Clause 30. The applicator head of any of clauses 23-30, further defining a cavity for receiving a portion of the skin of the subject, and in particular further comprising a suction orifice configured to be coupled to a pump for sucking air through the suction orifice.

Clause 31. The applicator head according to clause 23, wherein the electrode support is movable with respect to the cavity.

Clause 32. The applicator head of clause 30 or 31, further comprising a flexible lip arranged along a border of the cavity for sealing the cavity.

Clause 33. The applicator head of any of clauses 23-32, further comprising one or more mechanical fasteners to fix the applicator head to the skin.

Clause 34. The applicator head of clause 33, wherein the fasteners include one or more straps.

Clause 35. The applicator head according to any of clauses 23-34, further comprising a drive for moving the first electrode support.

Clause 36. An apparatus for treatment of a skin of a subject comprising one or more applicator heads according to any of clauses 23-35, and further comprising
an electrical power source for supplying electricity to at least the first electrode.

Clause 37. A method for treatment, particularly a cosmetic treatment, of a skin of a subject, comprising:
providing the apparatus according to clause 36;
attaching one or more of the applicator heads to a skin of the subject;
putting a portion of the skin and one or more applicator heads into contact;
activating the drive for moving the first electrode support; and
activating the electrical power source to supply RF energy to the skin.

Clause 38. The method of clause 37, wherein the second electrode is a passive electrode and is located on the skin of the subject.

Clause 39. The method of clause 37 or 38, wherein the second electrode has an opposite polarity from the first electrode polarity, the first and second electrodes form a first pair of electrodes and RF energy is applied to the skin through at least the first pair of electrodes.

Clause 40. The method of any of clause 39, wherein the second electrode is located in the applicator head including the first electrode.

Clause 41. The method of clause 39, wherein the second electrode is located in an applicator head different from the applicator head comprising the first electrode.

Clause 42. The method of any of clauses 37-41, further comprising:
interrupting the application of RF energy to a skin through the first pair of electrodes; and
applying RF energy to the skin through a second different pair of electrodes such that RF energy is applied at least to a partially different skin.

Clause 43. The method of any of clauses 37-42 further comprising:
joining a first and at least a second applicator heads.

Clause 44. The method of any of clauses 37-43, wherein at least two of the electrode supports move at the same speed, in particular at the same rotational speed.

Clause 45. The method of any of clauses 37-44, wherein a treatment time is between 10 and 60 minutes.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

What is claimed is:

1. An applicator head for use with an apparatus for treatment of a skin of a subject, the applicator head configured for being fixed to the skin of the subject and defining a cavity for receiving a portion of the skin of the subject comprising a suction orifice configured to be coupled to a pump for sucking air through the suction orifice, the applicator head further comprising:
a base,
a first RF electrode mounted on a first electrode support, wherein the first electrode support is movable with respect to the base,
a second RF electrode mounted on a second electrode support, and wherein the second electrode support is movable with respect to the base, and
a drive for moving the first electrode support with respect to the base, and wherein
the first and second electrode supports are operatively connected to each other such that when the drive moves the first electrode support, the second electrode support is also moved such that a distance between the first electrode and the second electrode is continuously varied in use.

2. The applicator head of claim 1, wherein the first electrode is eccentrically mounted on the first electrode support.

3. The applicator head of claim 1, further comprising a flexible lip arranged along a border of the cavity for sealing the cavity.

4. The applicator head of claim 1, further comprising one or more mechanical fasteners to fix the applicator head to the skin.

5. The applicator head of claim 4, wherein the fasteners include one or more straps.

6. A method for treatment of a skin of a subject, comprising:
attaching an applicator head to the skin of the subject,
introducing a portion of the skin of the subject into a cavity of the applicator head, by activating a pump configured to suck air through a suction orifice in the cavity, wherein the applicator head further comprises:
a base,
a first RF electrode, mounted on a first electrode support,
a second RF electrode mounted on a second electrode support, and
a drive for moving the first electrode support with respect to the base of the applicator head, and wherein
the first and second electrode supports are operatively connected to each other,
the method further comprising:
activating the drive to move the first electrode support, and thereby also move the second electrode such that a distance between the first electrode and the second electrode is continuously varied in use.

7. The method of claim 6, wherein the first electrode is eccentrically mounted on the first electrode support.

8. The method of claim 7, wherein the second electrode is eccentrically mounted on the second electrode support.

9. The method of claim 7, further comprising measuring an average skin temperature of a portion of the skin and adjusting the RF energy applied through the first and second electrodes based at least partially on the measured average skin temperature.

10. The method of claim 9, further comprising:
determining a reference average skin temperature between 40 and 50° C.; and
adjusting, by a control system, the RF energy applied through the first and second electrodes based on a measured average skin temperature to maintain the average skin temperature close to the reference average skin temperature.

11. The method of claim 10, wherein at least one of power and frequency of the RF energy is adjusted.

12. The method of claim 6, wherein the first and second electrode supports are moved rotationally, a rotational speed of each of the first and second electrode supports being in a range of 10 to 60 rpm.

13. A method for cosmetic treatment of a skin of a subject, comprising:
providing an apparatus with an electrical power source for supplying electricity and a first applicator head and a second applicator head, the first and second applicator heads being configured for being fixed to the skin of the subject and defining a cavity for receiving a portion of the skin of the subject, wherein the first and second applicator heads comprise a suction orifice configured to be coupled to a pump for sucking air through the suction orifices, and comprising a base, and wherein
the first applicator head comprises a first RF electrode mounted on a first electrode support that is movable with respect to the base of the first applicator head, and a first drive for moving the first electrode support with respect to the base, and wherein
the second applicator head comprises a second RF electrode;
attaching the first applicator head and the second applicator head to a skin of the subject;
putting a first portion of the skin and the first applicator head into contact and putting a second portion of the skin and the second applicator head into contact;
activating the first drive to continuously move the first electrode support of the first applicator head; and
activating the electrical power source to supply RF energy to the skin wherein the first electrode has a first polarity and the second electrode has a second polarity opposite the first polarity, the first and second electrodes form a first pair of electrodes and RF energy is applied to the skin through at least the first pair of electrodes.

14. The method of claim 13, further comprising:
interrupting the application of RF energy to a skin through the first pair of electrodes; and
applying RF energy to the skin through a second different pair of electrodes such that RF energy is applied at least to a third portion of the skin that is at least partially different than the first and second portions of the skin.

15. The method of claim 13, further comprising:
joining the first and the second applicator heads.

16. The method of claim 13, wherein the second RF electrode of the second applicator head is mounted on a second electrode support and is movable with respect to the base of the second applicator head and the second applicator head further comprises a drive to move the second electrode support with respect to the base, and the method further comprises activating the drive of the second applicator head for continuously moving the second electrode support of the second applicator head.

17. The method of claim 16, wherein a distance between the first electrode and a second electrode is continuously varied in use.

18. The method of claim 16, wherein the first and second electrode supports move at the same speed.

19. The method of claim 13, wherein a treatment time is between 10 and 60 minutes.

* * * * *